US009295705B2

(12) United States Patent
Chen et al.

(10) Patent No.: US 9,295,705 B2
(45) Date of Patent: Mar. 29, 2016

(54) TREATMENT FOR NEPHRITIS

(75) Inventors: Ann Chen, Xizhi (TW); Shuk-Man Ka, Xizhi (TW); Rey-Yuh Wu, Xizhi (TW); Jia-Ming Chang, Xizhi (TW)

(73) Assignee: DEVELOPMENT CENTER FOR BIOTECHNOLOGY, Taipei County (TW)

( * ) Notice: Subject to any disclaimer, the term of this patent is extended or adjusted under 35 U.S.C. 154(b) by 1119 days.

(21) Appl. No.: 13/290,519

(22) Filed: Nov. 7, 2011

(65) Prior Publication Data

US 2012/0114678 A1    May 10, 2012

Related U.S. Application Data

(60) Provisional application No. 61/411,000, filed on Nov. 8, 2010.

(51) Int. Cl.
| | |
|---|---|
| A61K 36/284 | (2006.01) |
| A61K 36/355 | (2006.01) |
| A61K 36/46 | (2006.01) |
| A61K 36/74 | (2006.01) |
| A61K 36/748 | (2006.01) |

(52) U.S. Cl.
CPC .............. *A61K 36/46* (2013.01); *A61K 36/284* (2013.01); *A61K 36/355* (2013.01); *A61K 36/748* (2013.01)

(58) Field of Classification Search
CPC .... A64K 36/46; A61K 36/748; A61K 36/355
See application file for complete search history.

(56) References Cited

U.S. PATENT DOCUMENTS

| | | | | |
|---|---|---|---|---|
| 2002/0031559 A1* | 3/2002 | Liang | ...................... | A61K 9/02 424/725 |
| 2010/0028318 A1* | 2/2010 | Saito | ..................... | A23K 1/1612 514/1.1 |
| 2011/0052731 A1* | 3/2011 | Park | ..................... | A61K 36/185 424/728 |

FOREIGN PATENT DOCUMENTS

| | | | |
|---|---|---|---|
| CN | 1054895 | * | 10/1991 |
| CN | 1300617 | * | 6/2001 |
| CN | 1326750 | * | 12/2001 |
| CN | 1768791 | * | 5/2006 |
| CN | 102406770 | * | 4/2012 |
| TW | I262793 | | 10/2006 |

OTHER PUBLICATIONS

Pei-Yi Tsai et al., Therapeutic potential of DCB-SLE1, an extract of a mixture of Chinese medicinal herbs, for severe lupus nephritis, Am J Physiol Renal Physiol, Oct. 2011, pp. F751-F764, vol. 301.
George C. Tsokos et al., Rewiring the T-cell: signaling defects and novel prospects for the treatment of SLE, Trends in Immunology, May 2003, pp. 259-263, vol. 24, No. 5.
Harini Bagavant et al., Pathogenesis of kidney disease in systemic lupus erythematosus, Curr Opin Rheumatol. Sep. 2009, pp. 489-494, vol. 21, No. 5.
Jose C. Crispin et al., Pathogenesis of human systemic lupus erythematosus: recent advances, Trends in Molecular Medicine, 2010, pp. 47-57, vol. 16, No. 2.
Melvin M. Schwartz et al., The prognosis and pathogenesis of severe lupus glomerulonephritis, Nephrology Dialysis Transplantation, 2008, pp. 1298-1306, vol. 23.
E. M. Tan et al., Deoxyribonucleic Acid (DNA) and Antibodies to DNA in the Serum of Patients with Systemic Lupus Erythematosus, Journal of Clinical Investigation, 1966, pp. 1732-1740, vol. 45, No. 11.
Bisram Deocharan et al., a-Actinin is a Cross-Reactive Renal Target for Pathogenic Anti-DNA Antibodies, The Journal of Immunology, 2002, pp. 3072-3078, vol. 168.
Lena Schiffer et al., Activated Renal Macrophages are Makers of Disease Onset and Disease Remission in Lupus Nephritis, The Journal of Immunology, 2008, pp. 1938-1947, vol. 180.
Tsuyoshi Takahashi et al., Natural killer T cells and innate immune B cells from lupus-prone NZB/W mice interact to generate igM and igG autoantibodies, Eur J Immunol., Jan. 2008, pp. 156-165, vol. 38, No. 1.
Defu Zeng et al., Subsets of Transgenic T Cells That Recognize CD1 Induce or Prevent Murine Lupus: Role of Cytokines, J. Exp. Med, Feb. 16, 1998, pp. 525-536, vol. 187, No. 4.
C. Molino et al., Clinical approach to lupus nephritis: Recent advances, European Journal of Internal Medicine, 2009, pp. 447-453, vol. 20.
C-S Yee et al., EULAR randomised controlled trial of pulse cyclophosphamide and methylprednisolone versus continuous cyclophosphamide and prednisolone followed by azathioprine and prednisolone in lupus nephritis, Ann Rheum Dis, 2003, pp. 525-529, vol. 63.
S. M. Benseler et al., Acute renal failure in paediatric systemic lupus erythematosus: treatment and outcome, Rheumatology, 2009, pp. 276-182, vol. 48.
Robert S. Flanc et al., Treatment of Diffuse Proliferative Lupus Nephritis: A Meta-Analysis of Randomized Controlled Trials, American Journal of Kidney Diseases, Feb. 2004, pp. 197-208, vol. 43, No. 2.
Gabor G. Illei et al., Combination Therapy with Pulse Cyclophosphamide plus Pulse Methylprednisolone Improves Long-Term Renal Outcome without Adding Toxicity in Patients with Lupus Nephritis, Annals of Internal Medicine, Aug. 21, 2001, pp. 248-257, vol. 135, No. 4.
Yuh-Chi Kuo et al., Regulation of Cell Proliferation, Gene Expression, Production of Cytokines, and Cell Cycle Progression in Primary Human T Lymphocytes by Piperlactam S Isolated from Piper kadsura, Molecular Pharmacology, 2000, pp. 1057-1066, vol. 58, No. 5, USA.

(Continued)

*Primary Examiner* — Chris R Tate
(74) *Attorney, Agent, or Firm* — WPAT, P.C.; Anthony King

(57) ABSTRACT

This invention relates to methods for treatment of nephritis. This invention further provides a method of treating with nephritis comprising administering to the subject an amount of herbal pharmaceutical composition thereof effective to treat the subject. Move particularly, this invention provides an herbal pharmaceutical composition comprising Rhizoma *Atractylodis macrocephalae, Eucommiae cortex, Lonicerae caulis*, and *Hedyotidis diffusae* Herba thereof for use in treating a subject afflicted with active nephritis.

16 Claims, 24 Drawing Sheets

(56) References Cited

OTHER PUBLICATIONS

Ruili Li et al., Enhancement of the immune responses to vaccination against foot-and-mouth disease in mice by oral administration of an extract made from Rhizoma Atractylodis Macrocephalae (RAM), Vaccine, 2009, pp. 2094-2098, vol. 27.

Hong Xu et al., Analysis of Trace Elements in Chinese Therapeutic Foods and Herbs, The American Journal of Chinese Medicine, 2009, pp. 625-638, vol. 37, No. 4.

Peter G. Tipping et al., T Cells in Crescentic Glomerulonephritis, Journal of the American Society of Nephrology, 2006, pp. 1253-1263, vol. 17.

Jan-Eric Turner et al., CCR6 Recruits Regulatory T Cells and Th17 Cells to the Kidney in Glomerulonephritis, J Am Soc Nephrol, 2010, pp. 974-985, vol. 21.

Lucie Roussel et al., IL-17 Promotes p38 MAPK-Dependent Endothelial Activation Enhancing Neutorphil Recruitment to Sites of Inflammation, The Journal of Immunology, 2010, ppl. 4531-4537, vol. 184.

Shiva Shahrara et al., IL-17-Mediated Monocyte Migration Occurs Partially through CC Chemokine Ligand 2/ Monocyte Chemoattractant Protein-1 Induction, The Journal of Immunology, 2010, pp. 4479-4487, vol. 184.

Claudio Costantini et al., Neutrophil activation and survival are modulated by interaction with NK cells, International Immunology, 2010, pp. 827-838, vol. 22, No. 10.

Shuk-Man Ka et al., Decoy Recepetor 3 Ameliorates an Autoimmune Crescentic Glomerulonephritis Model in Mice, J Am Soc Nephrol, 2007, pp. 2473-2485, vol. 18.

Vasileios C. Kyttaris et al., T lymphocytes in systemic lupus erythematosus: an update, Curr Opin Rheumatol, 2004, pp. 548-552, vol. 16.

Marco Tucci et al., Cytokine Overproduction, T-Cell Activation, and Defective T-Regulatory Functions Promote Nephritis in Systemic Lupus Erythematosus, Journal of Biomedicine and Bioetchnology, 2010, pp. 1-6, vol. 2010.

Jose C. Crispin et al., IL-17 in Systemic Lupus Erythematosus, Journal of Biomedicine and Biotechnology, pp. 1-4, vol. 2010.

Mo Yin Mok et al., The Relation of Interleukin 17 (IL-17) and IL-23 to Th1/Th2 Cytokines and Disease Activity in Systemic Lupus Erythematosus, The Journal of Rheumatology, 2010, pp. 2046-2052. vol. 37, No. 10.

Kamini Shah et al., Dysregulated balance of Th17 and Th1 cells in systemic lupus erythematosus, Arthritis Research & Therapy, 2010, pp. 1-10, vol. 12, R. 53.

Natalya Seredkina et al., Progression of Murine Lupus Nephritis is Linked to Acquired Renal Dnase1 Deficiency and Not to Up-Regulated Apoptosis, The American Journal of Pathology, Jul. 2009, pp. 97-106, vol. 175, No. 1.

W.-S. Uhm et al., Cytokine balance in kidney tissue from lupus nephritis patients, Rheumatology, 2003, pp. 935-938, vol. 42.

H.-A. Shui et al., LPS-evoked IL-18 expression in mesangial cells plays a role in accelerating lupus nephritis, Rheumatology, 2007, pp. 1277-1284, vol. 46.

Dong Guangfu et al., IL-17 induces autoantibody overproduction and peripheral blood mononuclear cell overexpression of IL-6 in lupus nephritis patients, Chinese Medical Journal, 2003, pp. 543-548, vol. 116, No. 4.

MM Schwartz et al., Evidence of concurrent immunopathological mechanisms determining the pathology of severe lupus nephritis, Lupus, 2009, pp. 149-158, vol. 18.

Hyekyung Ha et al., Effects of Eucommiae Cortex on Osteoblast-like Cell Proliferation and Osteoclast Inhibition, Archives of Pharmacal Research, 2003, pp. 929-936, vol. 26, No. 1.

\* cited by examiner

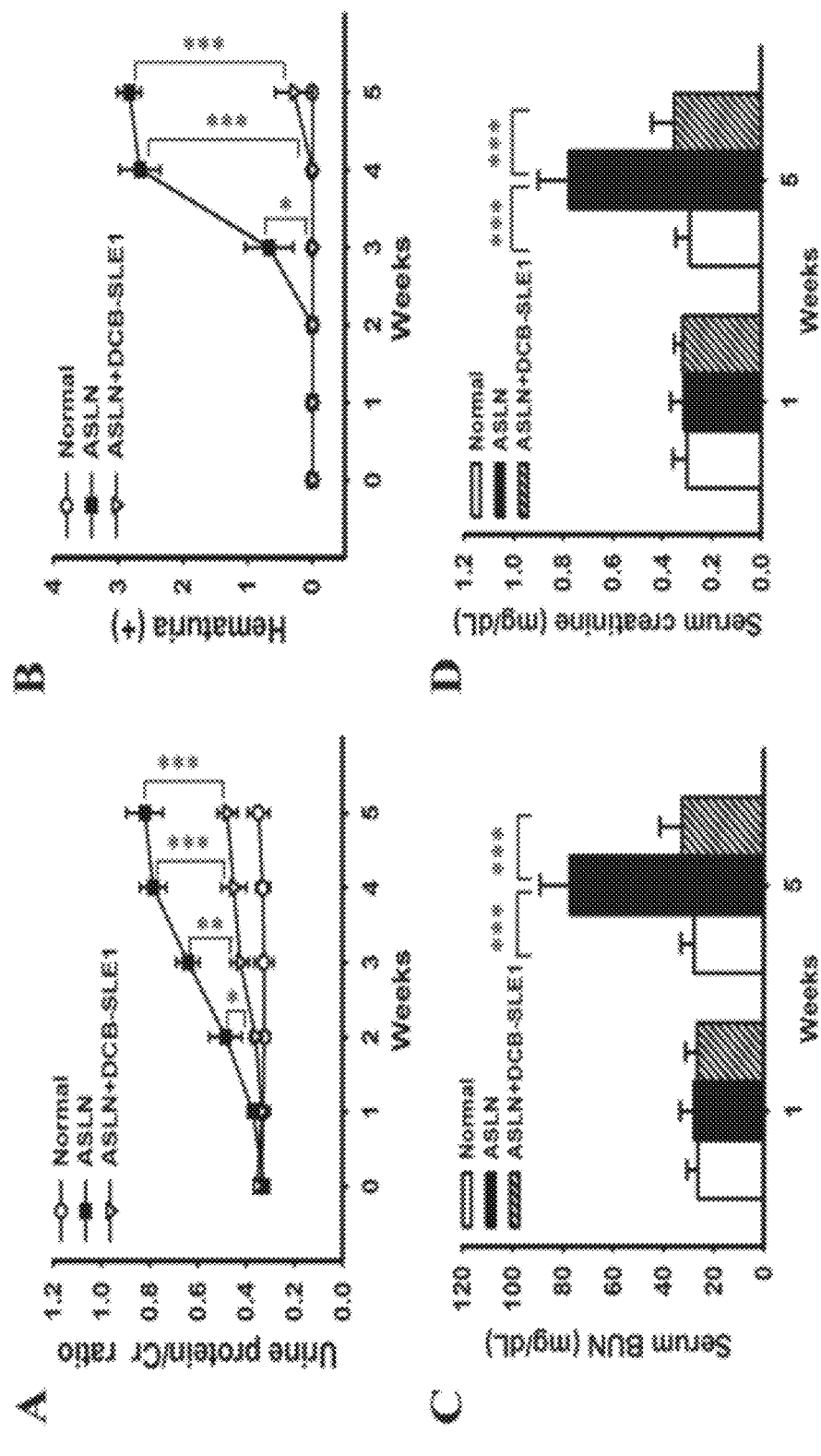
FIGURE 1 (A)-(D)

FIGURE 2 (B)-(D)
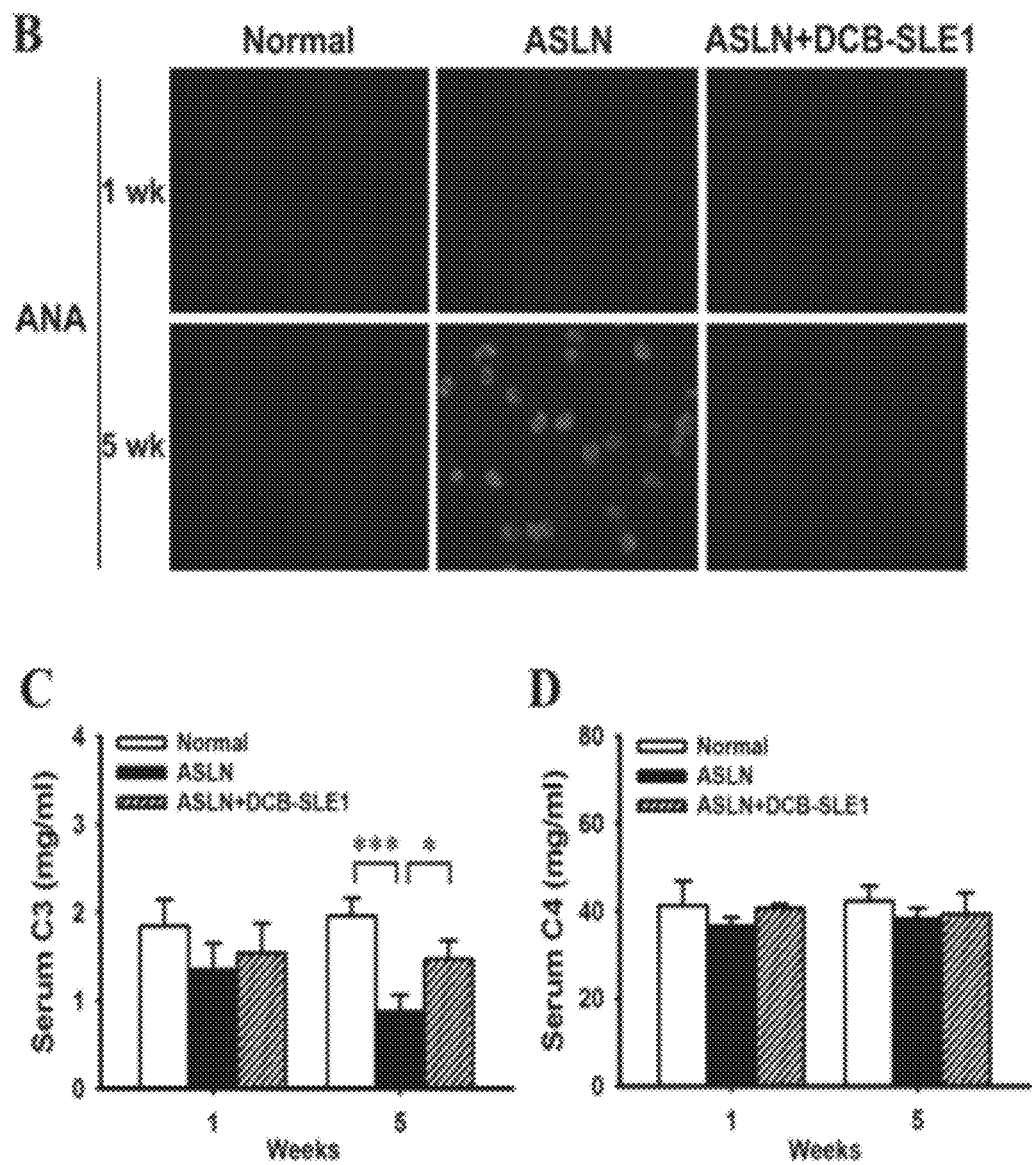

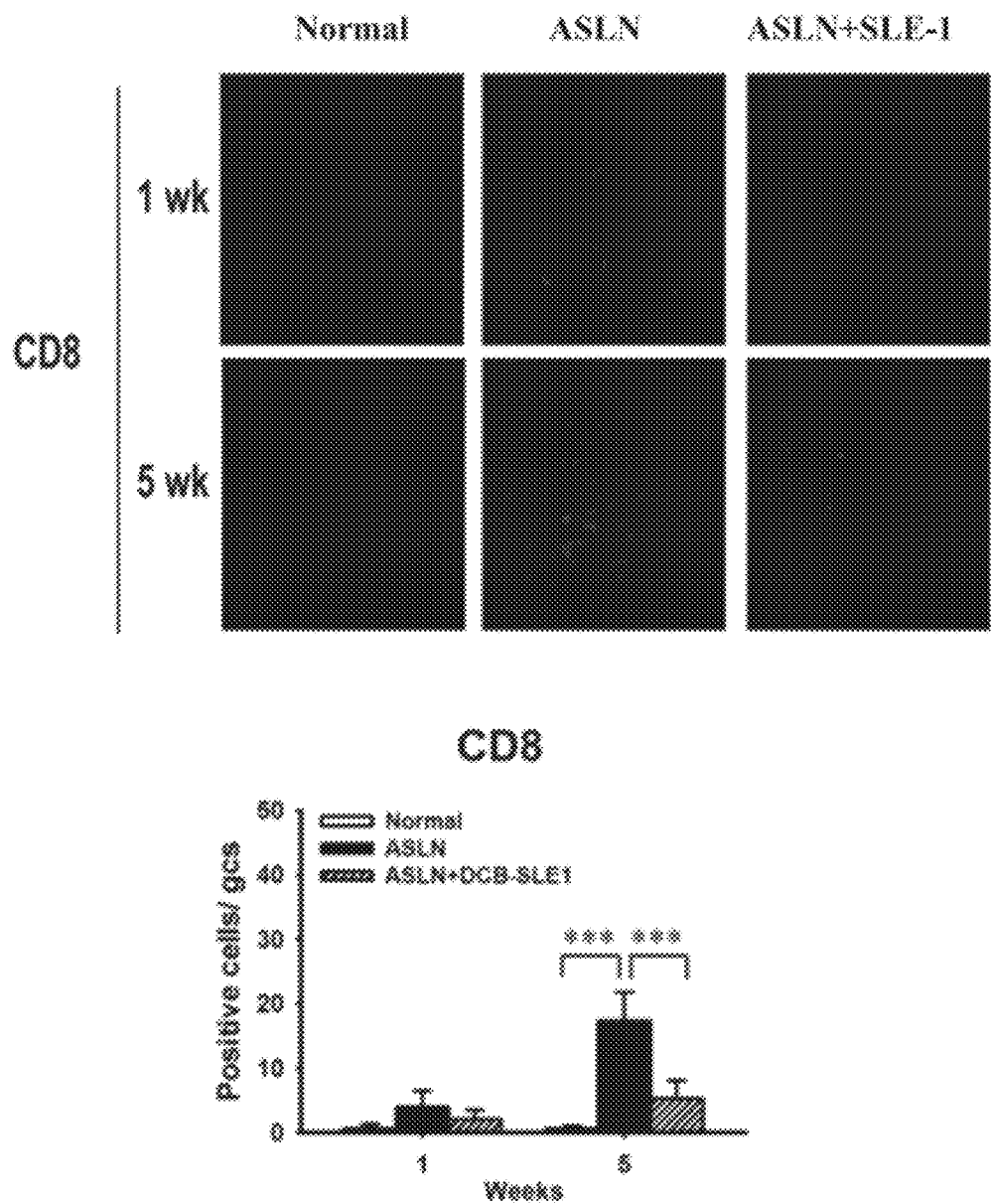

FIGURE 7 (A)-(D)
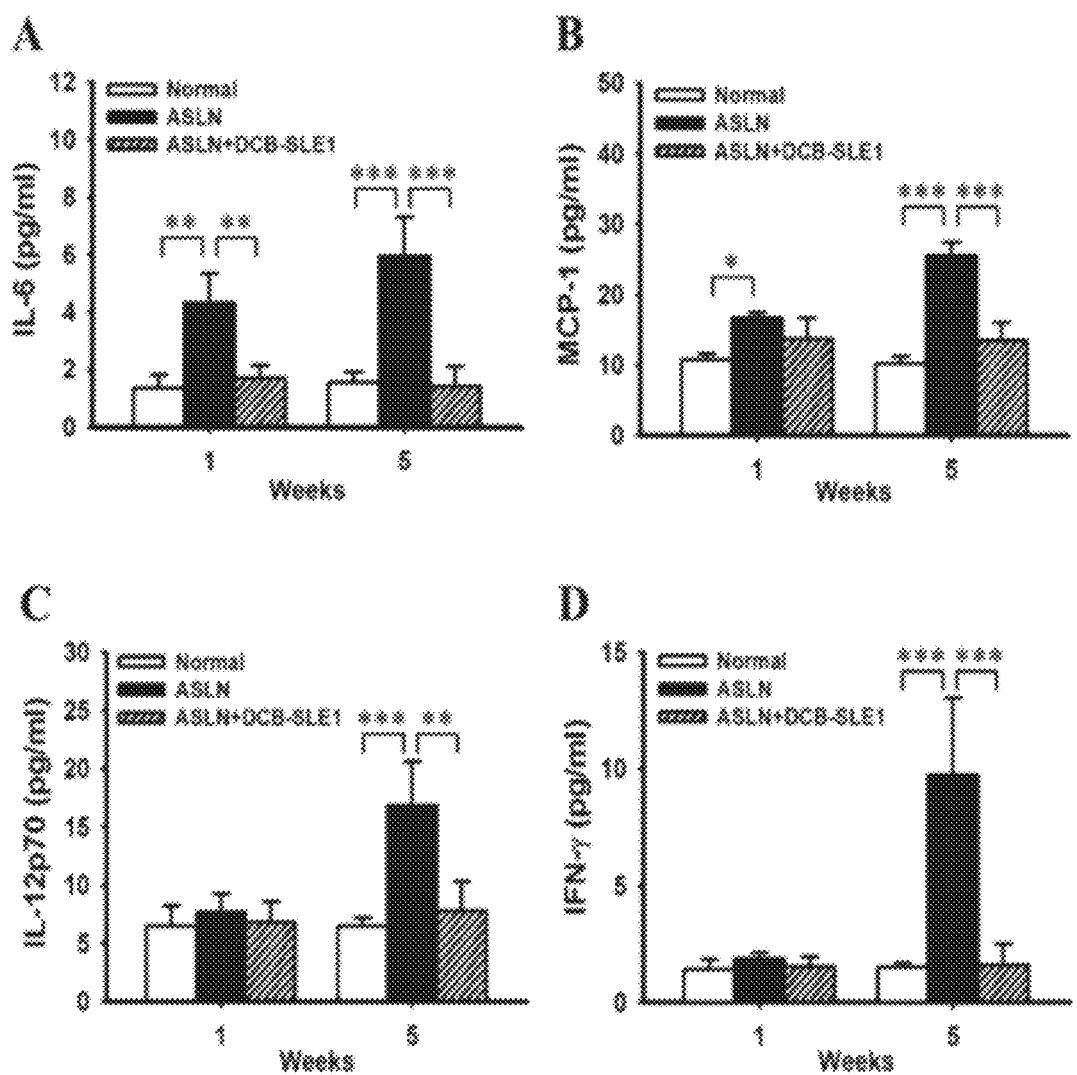

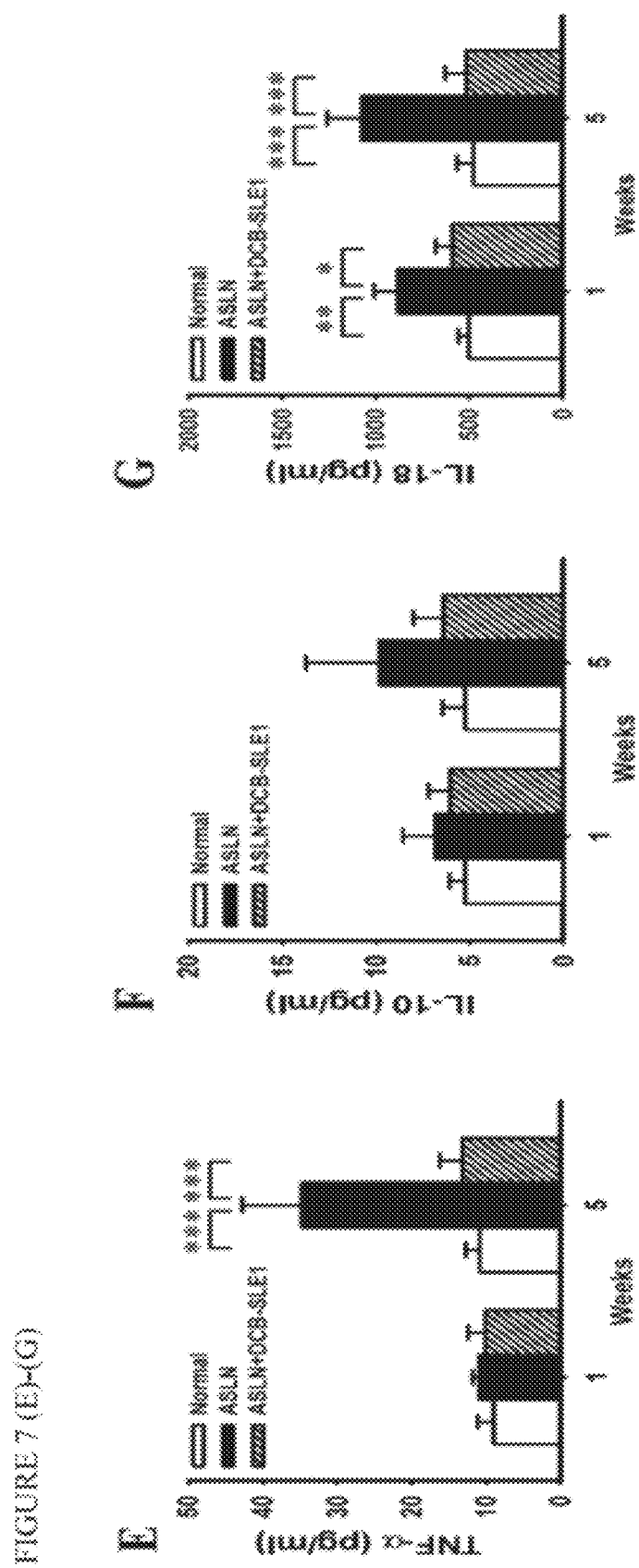
FIGURE 7 (E)-(G)

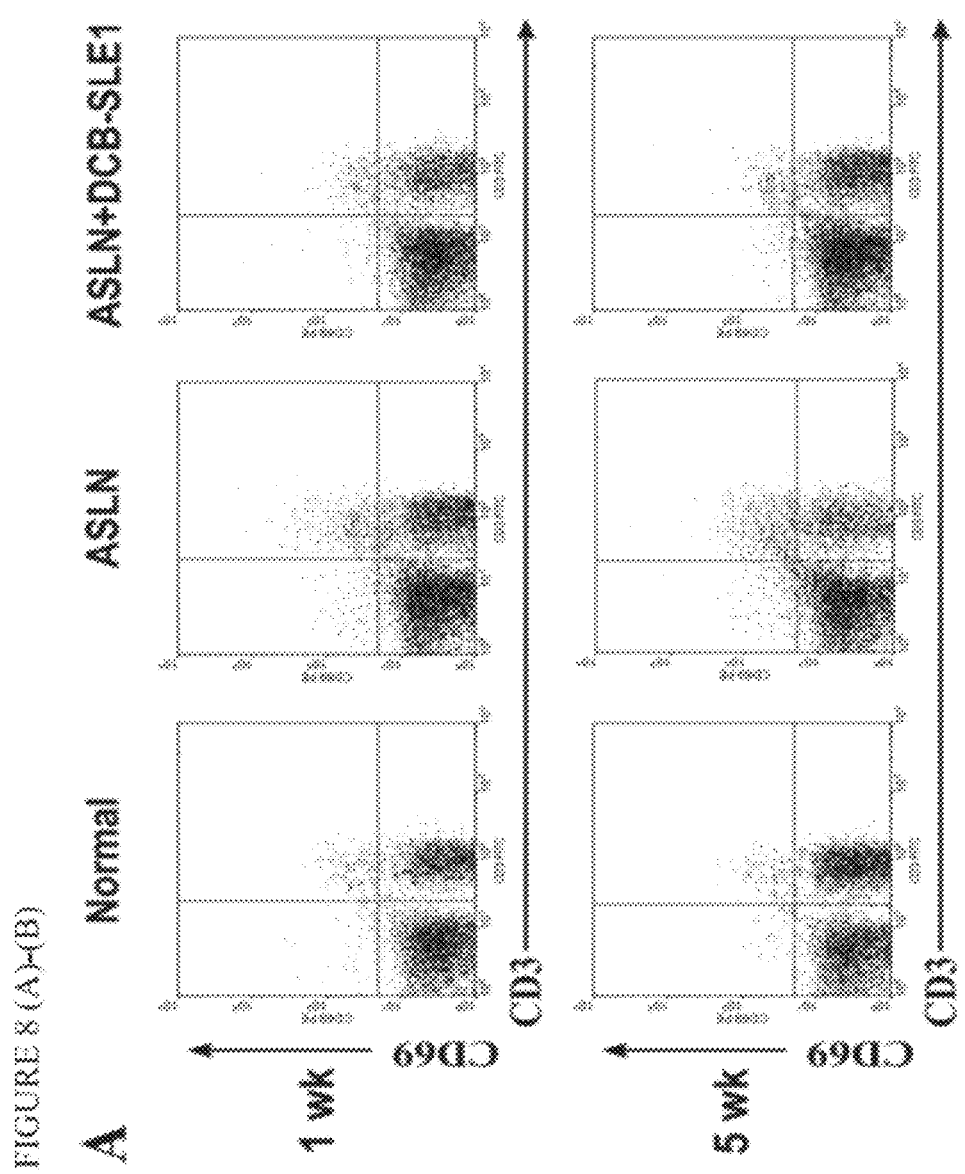
FIGURE 8 (A)-(B)

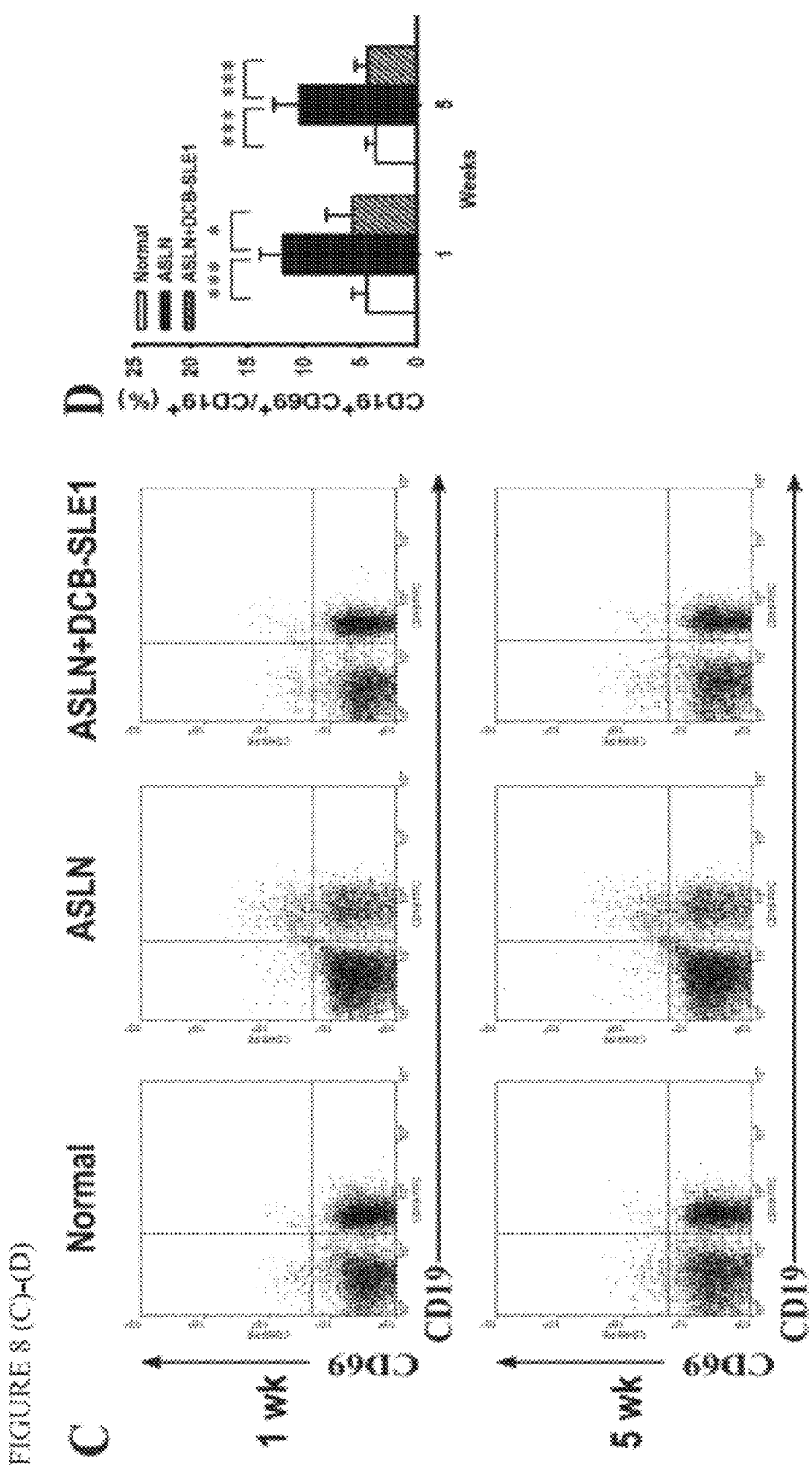

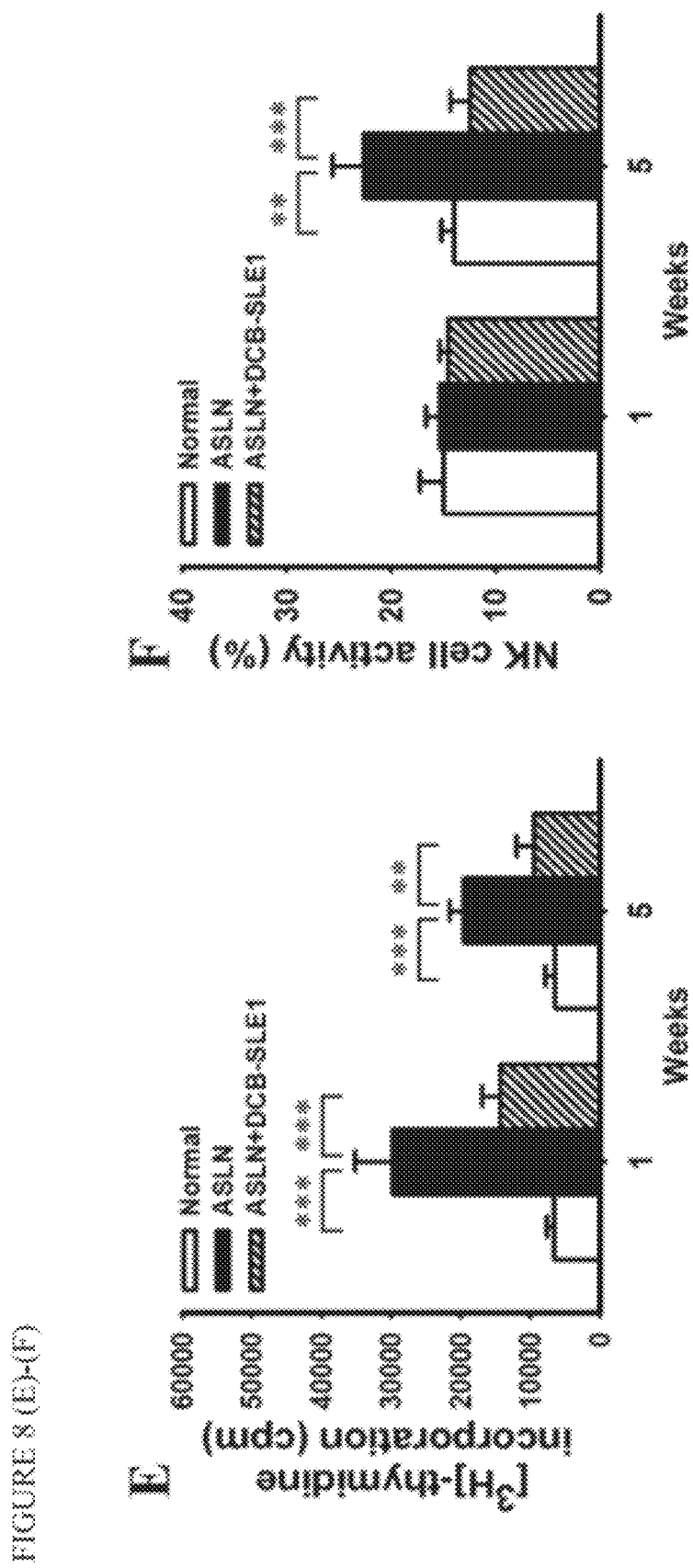
FIGURE 8 (E)-(F)

FIGURE 9 (A)-(B)
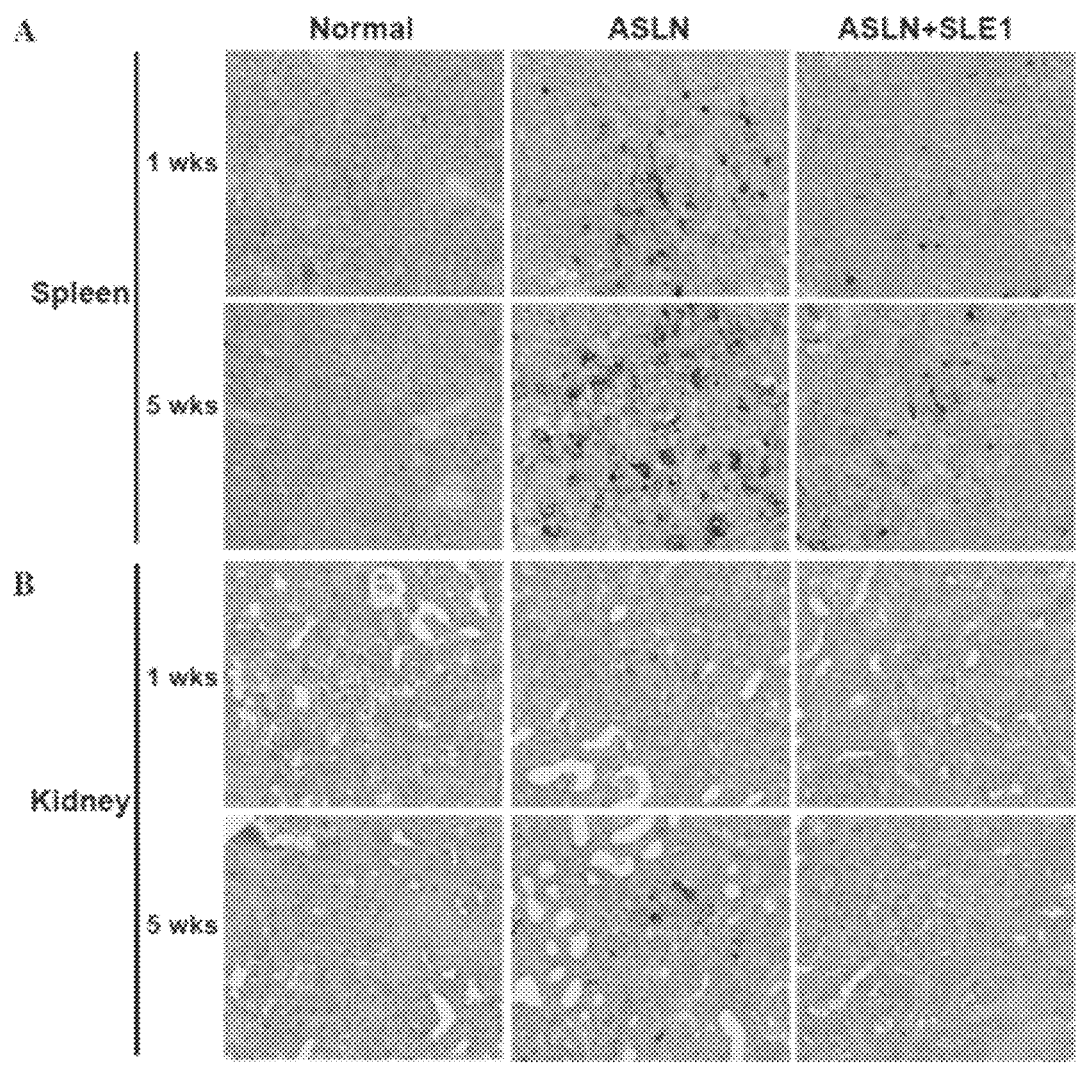

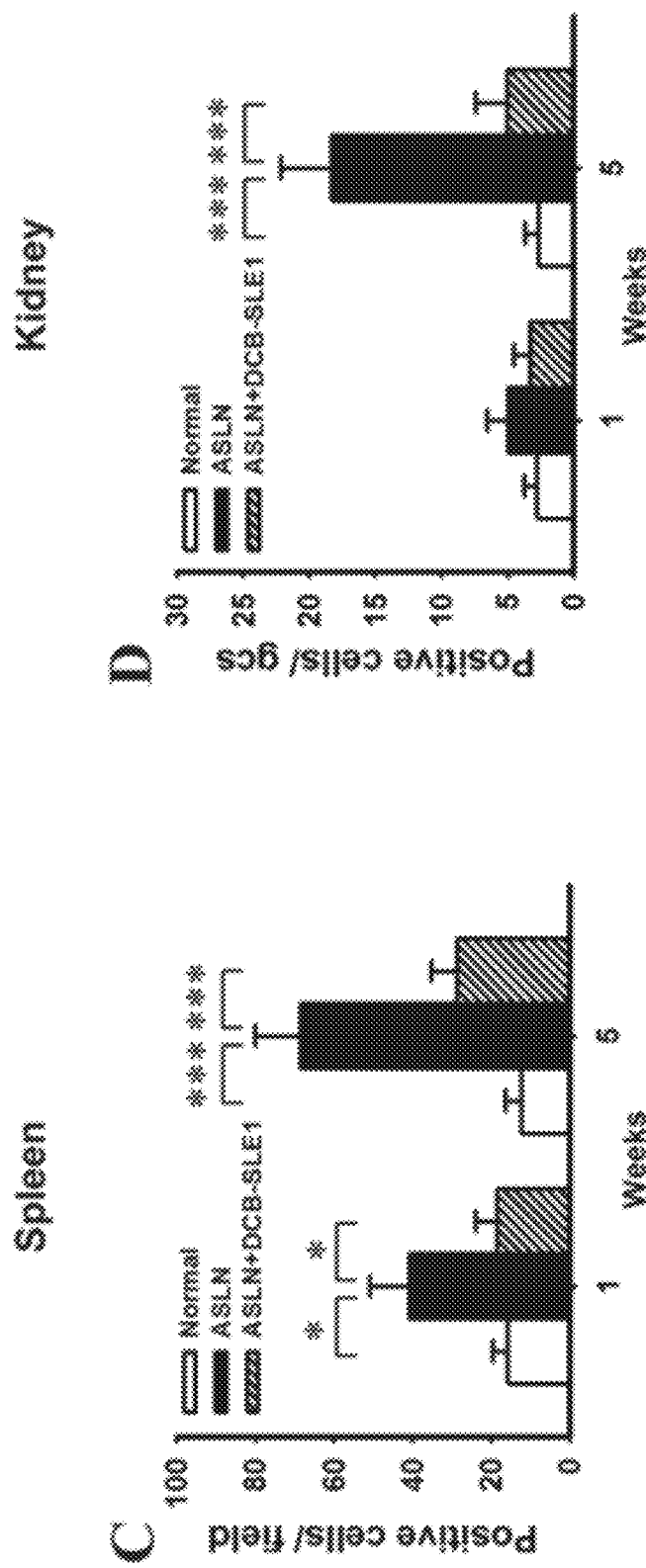
FIGURE 9 (C-D)

TREATMENT FOR NEPHRITIS

This application claims the benefit of U.S. Provisional Application No. 61/411,000 filed on Nov. 8, 2010, the entire content of which is hereby incorporated by reference herein. Throughout this application, one publication (*Am J Physiol Renal Physiol*, 301: F751-F764, 2011) by same author in one year is also referred.

FIELD OF THE INVENTION

This invention relates to methods for treatment of nephritis. This invention further provides a method of treating with nephritis comprising administering to the subject an amount of herbal pharmaceutical composition thereof effective to treat the subject. Move particularly, this invention provides an herbal pharmaceutical composition comprising Rhizoma *Atractylodis macrocephalae*, *Eucommiae cortex*, *Lonicerae caulis*, and *Hedyotidis diffusae* Herba thereof for use in treating a subject afflicted with active nephritis.

DESCRIPTION OF PRIOR ART

Lupus nephritis (LN), characterized by inflammation of the kidney, is a complication which occurs in a subpopulation of patients with systemic lupus erythematosus (SLE) and is one of the most serious complications caused by systemic lupus erythematosus. Systemic lupus erythematosus is an autoimmune disorder involving multiple organs injury due to autoantibody production and aberrant immune responses with excessive and uncontrolled T cell (*Trends Immunol*, 24: 259-263, 2003), associated with various complications including lupus nephritis (*Curr Opin Rheumatol*, 21: 489-494, 2009; *Trends Mol Med*, 16: 47-57, 2010).

Lupus nephritis usually arises early in the disease course, and the pathogenesis of lupus nephritis is believed to derive from deposition of immune complexes in the kidney glomeruli that initiates an inflammatory response.

Severe lupus nephritis is an extremely progressive form of lupus nephritis showing histological changes of cellular crescents, fibrinoid necrosis, extensive interstitial inflammation, and tubular atrophy, and which is associated with significant morbidity and mortality. Systemic immunity disorder association with autoantibody production and inflammation plays an important role in disease progression in lupus nephritis. In lupus nephritis, autoantibodies of multiple specificities participating in the formation of immune complexes deposition in the kidneys were believed to be the primary mediators of renal disease (*Curr Opin Rheumatol*, 21: 489-494, 2009; *J Clin Invest*, 45: 1732-1740, 1966; *J Immunol*, 168: 3072-3078, 2002). Renal infiltration by T cells, neutrophils, and monocytes/macrophages have a dominant role in the progression of severe lupus nephritis (*Nephrol Dial Transplant*, 23: 1298-1306, 2008; *Lupus*, 18: 149-158, 2009; *J Immunol*, 180: 1938-1947, 2008). In addition, new insights on the impaired natural killer (NK) cell cytotoxicities to promote renal lesions in lupus nephritis have been discovered (*Eur J Immunol*, 38: 156-165, 2008; *J Exp Med*, 187: 525-536, 1998).

There is no definitive treatment or cure for nephritis or lupus nephritis. The principal goals of therapy is to normalize renal function, urine sediment and proteinuria, reduce the frequency of relapses or prevent the progressive loss of renal function through mild, moderate and severe renal impairment to end stage renal disease requiring dialysis or kidney transplantation. The current therapy for severe lupus nephritis is still using combine corticosteroids with other cytotoxic agents or immunomodulators such as cyclophosphamide, azathioprine or ciclosporin (*Eur J Intern Med*, 20: 447-453, 2009; *Ann Rheum Dis*, 63: 525-529, 2004; *Rheumatology (Oxford)*, 48: 176-182, 2009), and many of them are found have various side effects (*Am J Kidney Dis*, 43: 197-208, 2004; *Ann Intern Med*, 135: 248-257, 2001). Most of the above mentioned treatments are not specifically indicated for the treatment of lupus nephritis and treatment protocols vary. There is, therefore, a need for alternative therapies with better risk-benefit profiles for the treatment of nephritis or lupus nephritis. Traditional Chinese herbs are now widely acknowledged for their immunomodulatory and antitumor activities (*Mol Pharmacol*, 58: 1057-1066, 2000).

DCB-SLE1 is a mixture extract of four traditional Chinese medicine which has been suggested as an oral formulation for the treatment of systemic lupus erythematosus. DCB-SLE1 can reduce the formation of serum double-stranded DNA (dsDNA) and the levels of urine protein is described in Taiwan Patent Application No. I262,793. The use of DCB-SLE1 for systemic lupus erythematosus had been previously suggested in '793 patent. The composition of DCB-SLE1 and the process for preparing the same are also described in '793 patent, which is hereby incorporated by reference into this application. However, the effects of DCB-SLE1 on nephritis have not been disclosed. The '793 patent does not disclose the use of DCB-SLE1 for nephritis.

In the present invention, the inventors have surprisingly found that DCB-SLE1 is particularly effective for the treatment of nephritis. The inventors investigated the effects of DCB-SLE1 on the ASLN especially the pathogenic role of systemic immunity associated with abnormal T/B cells leading autoantibody production and inflammation, which have been widely considered as a major mechanism responsible for widespread severe renal lesions characteristic of severe lupus nephritis.

BRIEF DESCRIPTION OF THE DRAWINGS

FIG. 7 shows that DCB-SLE1 decreases serum levels of inflammatory cytokines. (A) IL-6. (B) MCP-1. (C) IL-12p70. (D) IFN-γ. (E) TNF-α. (F) IL-10. (G) IL-18. Data are mean±SEM for six mice per group. *p<0.05, p<0.01, *p<0.005.

FIG. 8 shows that DCB-SLE1 modulates systemic immunity. Immunofluorescence dot-plot pattern of the CD69 activation marker on $CD3^+$ T cells (A) or $CD19^+$ B cells (C). Percentage of $CD3^+CD69^+$ T cells (B) and $CD19^+CD69^+$ (D). (E) T cell proliferation. (F) NK cells activity. Each bar represents the mean±SEM for six mice per group. *p<0.05, p<0.01, *p<0.005.

FIG. 9 shows that DCB-SLE1 inhibits apoptosis in the kidney and spleen. Detection of apoptosis by terminal deoxynucleotidyl transferase-mediated dUTP nick-end labeling (TUNEL) in spleen (A) and kidney (B). Original magnification, 400×. Scoring of positive cells in spleen (C) and kidney (D). Data are mean±SEM for six mice per group. *p<0.05, p<0.01, *p<0.005.

SUMMARY OF THE INVENTION

Figure 1:
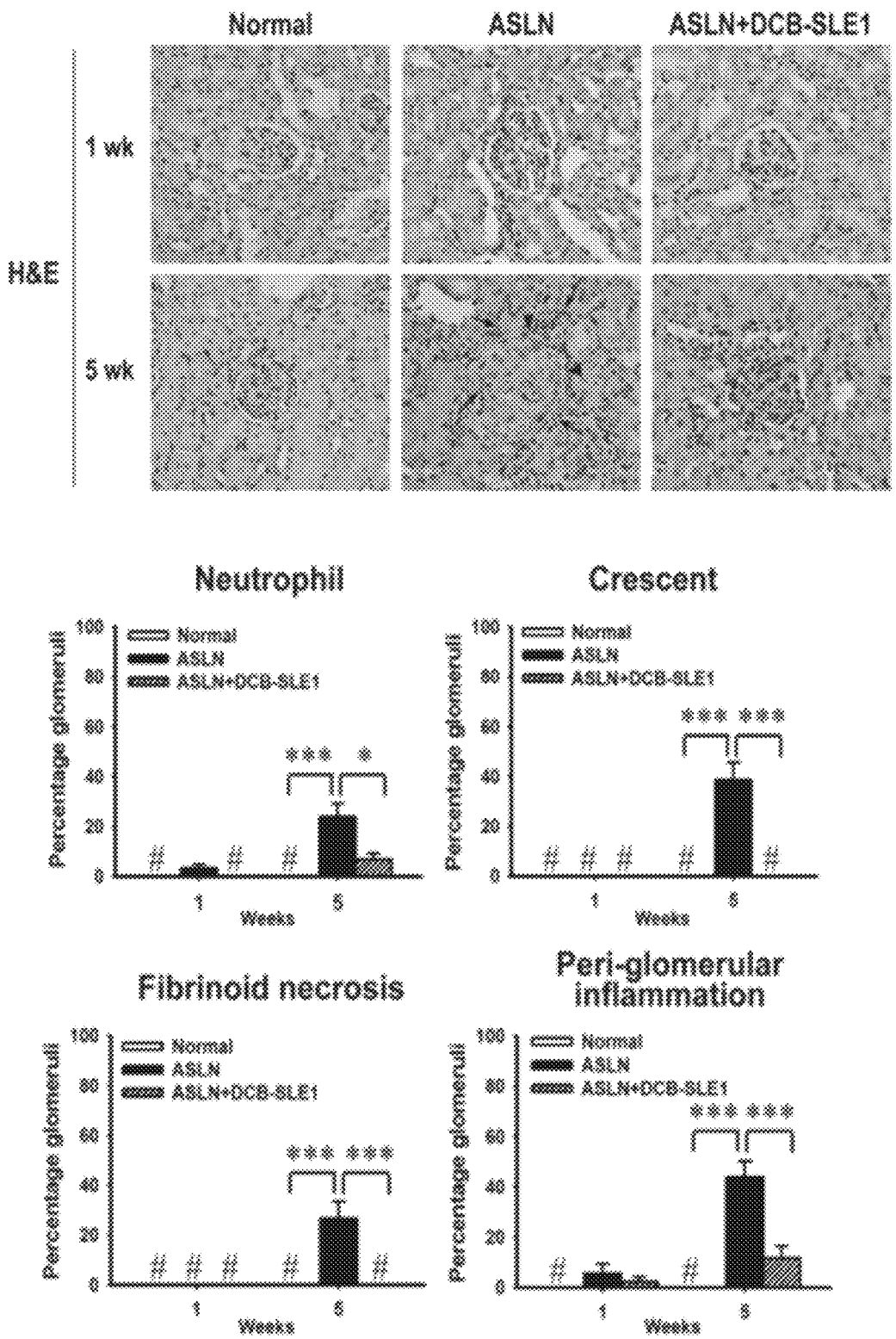
FIG. 1 shows that DCB-SLE1 administration significantly ameliorates proteinuria, hematuria, renal function, and severe renal lesions in ASLN model. (A) Time-course studies of urine protein. (B) Time-course studies of hematuria. (C) Serum blood urea nitrogen (BUN) levels. (D) Serum creatinine levels. (E) Detection of kidney histopathological evaluation by H&E staining. The arrow head and black arrow indicate the crescent formation and hyaline thrombi, respectively. Original magnification, 400×. Semiquantificative analysis of kidney histopathological change is shown in lower panel. Data are mean±SEM for six mice per group. *$p<0.05$, $p<0.01$, *$p<0.005$, #Not detectable.

The present invention firstly provides a method of treating a subject afflicted with nephritis, which comprises administering to the subject an herbal pharmaceutical composition comprising: a Rhizoma *Atractylodis Macrocephalae*; a *Eucommiae Cortex*; a *Lonicerae Caulis*; and a *Hedyotidis Diffusae* Herba.

The present invention also provides a method of preparation of the herbal pharmaceutical composition of claim 1 comprising the following steps:
(1) providing a mixture consisting of the Rhizoma *Atractylodis Macrocephalae*, *Eucommiae Cortex*, *Lonicerae Caulis* and *Hedyotidis Diffusae* Herba at an equal weight ratio;
(2) adding water followed by soaking the mixture;
(3) heating the resulting mixture to prepare a hot-water extract;
(4) filtering said water extract to obtain a filtrate; and
(5) concentrating and evaporating the filtrate under reduced pressure to generate a herbal composition.

DETAILED DESCRIPTION OF THE INVENTION

As used herein, the terms "including", "containing" and "comprising" are used herein in their open, non-limiting sense.

The term "DCB-SLE1" used herein refers to an extract of a mixture of four traditional Chinese medicinal herbs, Rhizoma *Atractylodis macrocephalae*, *Eucommiae cortex*, *Lonicerae caulis*, and *Hedyotidis diffusae* Herba, developed by the Development Center for Biotechnology (Taipei, Taiwan, ROC) and approved as an investigational new drug by the Department of Health, Taiwan. DCB-SLE1 have been used empirically for the treatment of proteinuria in Taiwan, and is currently being investigated in a double-blind, randomized, parallel, placebo-controlled phase I/II clinical trial to evaluate the safety and efficacy in systemic lupus erythematosus patients.

As disclosed herein, "Rhizoma *Atractylodis Macrocephalae*" or "RAM" refers to a kind of traditional Chinese herbal, a genus of *Compositae*, which is used as a diuretic agent in patients. In modern scientific research, RAM can enhance the vaccination of foot-and-mouth disease in mice (*Vaccine*, 27: 2094-2098, 2009).

As disclosed herein, "*Eucommiae Cortex*" refers to a kind of traditional Chinese herbal, which is used as anti-inflammatory agent to improve the symptom of liver inflammation. Recent research demonstrates that *Eucommiae* Cortex containing geniposidic acid, geniposide and aucubin elicit their effects on anti-osteoporosis (*Arch Pharm Res*, 26: 929-936, 2003).

As disclosed herein, "*Lonicerae Caulis*" refers to a kind of traditional Chinese herbal, which is used as anti-inflammatory agent for relief of pain. It is reported that increase the phagocytic activity of neutrophil (*Am J Physiol Renal Physiol*, 301: F751-F764, 2011).

As disclosed herein, "*Hedyotidis Diffusae* Herba" refers to a kind of traditional Chinese herbal, which is traditionally used as anti-inflammatory agents for reducing abscess, toxic sores, ulcerations, swellings and snakebite. *Hedyotidis Diffusae* has been reported that contains high level of Lanthanum for treating cardiovascular disorder (*Am J Chin Med*, 37: 625-638, 2009).

As used herein, the term "adaptive immune system" refers to highly specialized, systemic cells and processes that eliminate pathogenic challenges. The cells of the adaptive immune system are a type of leukocyte, called a lymphocyte. B cells and T cells are the major types of lymphocytes.

The term "B cells" refers to a group of white blood cells known as lymphocytes, which play a central role in antibody production. B cells are produced in the bone marrow The term "T cells" refer to a group of white blood cells known as lymphocytes, which play a central role in cell-mediated immunity. T cells can be distinguished from other lymphocyte types, such as B cells and NKs by the presence of a special receptor on their cell surface called the T cell receptor (TCR).

The term "natural killer" or "NK" refers to a class of lymphoid cells which are activated by interferons to contribute to innate host defense against viruses and other intracellular pathogens.

As used herein, "treating" encompasses, e.g., inducing inhibition, regression, or stasis of a disorder, or lessening, suppressing, inhibiting, reducing the severity of, eliminating, or ameliorating a symptom of the disorder.

As used herein, "inhibition" of disease progression or disease complication in a subject means preventing or reducing the disease progression and/or disease complication in the subject.

Accordingly, the present invention provides a method of treating a subject afflicted with nephritis, which comprises administering to the subject an herbal pharmaceutical composition comprising: a Rhizoma *Atractylodis Macrocephalae*; a *Eucommiae Cortex*; a *Lonicerae Caulis*; and a *Hedyotidis Diffusae* Herba.

In one embodiment of the method, the subject is a mammal on an accelerated severe lupus nephritis (ASLN) model, which characterized by acute onset of proteinuria, azotemia, autoantibody production, and development of severe nephritis. The accelerated severe lupus nephritis model is induced by twice weekly injection with bacterial lipopolysaccharide (LPS), which is a *Salmonella* type lipopolysaccharide.

In one embodiment of the method, the herbal pharmaceutical composition (DCB-SLE1) is administered at a daily dosage at 12.5 g/kg body weight of the subject. And the DCB-SLE1 is administered daily for the first 2 days after the first injection of lipopolysaccharide.

The present invention evaluated the therapeutic effects of DCB-SLE1 on an accelerated and severe lupus nephritis in mice induced by injecting *Salmonella* type lipopolysaccharide in New Zealand black/white F1 mice, and the mice were daily administered by gavage with DCB-SLE1 at two days after the first dose of lipopolysaccharide till the mice were sacrificed at week 1 and week 5, respectively. The present invention provides a method of treating nephritis in a subject and verifying the effects of DCB-SLE1 on the subject. DCB-SLE1 administration effectively mitigated the evolution of the subject by averting proliferation, crescent formation, neutrophils infiltration, and interstitial inflammation, involving a key mechanism of suppression B cell activation and decreased autoantibody production, suppression T cell activation including NK cell activity, prevention inflammation via blocking systemic inflammatory cytokines expression and intra-renal nuclear factor (NF)-κB activation.

In one embodiment of the method, the herbal pharmaceutical composition is capable of specifically reducing proteinuria, hematuria, renal function defects, and severe renal lesions in a subject. The results showed that DCB-SLE1 administration significantly ameliorates proteinuria, hematuria, renal disfunction, and severe renal lesions including neutrophil infiltration, crescent formation, fibrinoid necrosis, and interstitial inflammation.

In one embodiment of the method, the herbal pharmaceutical composition is capable of specifically reducing autoantibody in serum and immune deposits in the kidney of a subject.

In one embodiment of the method, the herbal pharmaceutical composition is capable of specifically inhibiting of renal infiltration of T cells, monocytes/macrophages, and neutrophils in a subject.

It is well known that inappropriate or unbalanced T cell responses are supposed to initiate and perpetuate glomerular and tubulointerstitial tissue damage in severe lupus nephritis either directly by cytotoxic functions or cytokine secretion or indirectly by providing help for induction of autoantibodies and cytokines or immune complexes or by activating macrophages and neutrophils (*J Am Soc Nephrol,* 17: 1253-1263, 2006; *J Am Soc Nephrol,* 21: 974-985, 2010). The present invention showed that DCB-SLE1 administration significantly inhibited TB cell activation and T cell proliferation in ASLN+DCB-SLE1 mice as early as week 1 and that these effects were maintained up to at least week 5. These effects were closely associated with a significant reduction in serum autoantibody levels and glomerular immune deposits.

In one embodiment of the method, the herbal pharmaceutical composition is capable of specifically decreasing IL-6, IL-17A, and IL-18 mRNA levels in the kidney of a subject.

In one embodiment of the method, the herbal pharmaceutical composition is capable of inhibiting renal IL-6 and MCP-1 protein expression and NF-κB activation in a subject.

In one embodiment of the method, the herbal pharmaceutical composition is capable of decreasing serum levels of inflammatory cytokines. And the inflammatory cytokines is selected from the group consisting of IL-6, MCP-1, IL-12p70, IFN-γ, TNF-α, and IL-18.

The data showed that DCB-SLE1 administration capable of significantly reducing the serum levels of IFN-γ, IL-6, and IL-12p70, as well as suppressing the renal expression levels of IL-6, IL-17A and IL-18 mRNA in the ASLN model, suggesting that DCB-SLE1 might benefit the animals via in part blocking a Th1 bias response. In addition, IL-17 has a potent proinflammatory effect in association with functional recruitment of neutrophils and macrophages in the site of inflammation via overexpression of IL-8 and MCP-1 (*J Immunol,* 184: 4531-4537, 2010; *J Immunol,* 184: 4479-4487, 2010). Similarly, IL-18 has been shown to prolonged neutrophils survival in patients and in vitro (*Int Immunol,* 22: 827-838, 2010). The present invention further confirms that DCB-SLE1 can inhibit neutrophils infiltration in the kidney in part by a dramatic reduction of renal both IL-17 and IL-18 expression.

In one embodiment of the method, the herbal pharmaceutical composition is capable of modulating cellular immune responses in a subject. NK T cells have been shown to contribute to the development of lupus in NZB/W mice by helping B cells to secrete autoantibodies in vitro (*Eur J Immunol,* 38: 156-165, 2008; *J Exp Med,* 187: 525-536, 1998). NK cells develop in lymphoid tissue and can be found in close proximity to T cells, where they can affect adaptive immune responses, with possible implications for autoimmune adaptive responses. The present invention demonstrated that DCB-SLE1 administration significantly inhibited the increase in NK cell activity in ASLN mice at week 5 and significantly suppressed serum levels of IFN-γ. These results suggest that the effects of DCB-SLE1 on NK cell activity may contribute to the attenuation of ASLN.

In one embodiment of the method, the herbal pharmaceutical composition is capable of preventing apoptosis in the kidney and spleen of a subject. The present invention showed DCB-SLE1 presented protecting apoptosis effect both in systemic (spleen) and local (kidney). The data provided that blocking of apoptosis in the kidney was associated with lower histological severity of the renal lesions in ASLN. Inhibition of apoptosis in lymphoid tissues (as represented by the spleen) and in the kidney is very likely linked to the beneficial effects of DCB-SLE1 in ACLN.

The present invention demonstrated that DCB-SLE1 administration significantly prevented T cells, monocytes/macrophages, and neutrophils infiltration in kidney tissues and block NF-κB activity in the kidney, contributing to the prevention of interstitial inflammation. These effects operating locally in the kidney to suppress inflammatory cells infiltrations could serve as an immediate and crucial mechanism for the beneficial. This invention provides the first demonstration that DCB-SLE1, which consists of Rhizoma *Atractylodis Macrocephalae, Eucommiae Cortex, Lonicerae Caulis,* and *Hedyotidis Diffusae* Herba., can significantly ameliorate the severity of pathology in ASLN model. Mechanistic analyses revealed that DCB-SLE1 administration: (1) modulation of cellular and humoral immunity, including suppression of TB cell activation and T cell proliferation and inhibition of NK cell activity; (2) inhibition of renal inflammation by suppression of Th1 and Th17 cytokine production and NF-κB activation; and (3) prevention of apoptosis in the kidney and lymphoid tissues (e.g., spleen). Based on these findings, the present invention proposed that DCB-SLE1 is capable of protecting the kidney from autoimmune-mediated acute and severe damage through systemic immune modulation and anti-inflammation pathways.

Accordingly, the present invention provides a method of preparation of the herbal pharmaceutical composition comprising a Rhizoma *Atractylodis Macrocephalae*; a *Eucommiae Cortex*; a *Lonicerae Caulis*; and a *Hedyotidis Diffusae* Herba comprises the following steps:

(1) providing a mixture consisting of the *Rhizoma Atractylodis Macrocephalae, Eucommiae Cortex, Lonicerae Caulis* and *Hedyotidis Diffusae* Herba at an equal weight ratio;
(2) adding water followed by soaking the mixture;
(3) heating the resulting mixture to prepare a hot-water extract;
(4) filtering said water extract to obtain a filtrate; and
(5) concentrating and evaporating the filtrate under reduced pressure to generate a herbal composition.

In one embodiment of the method, the heating in step (3) is performed at a temperature of 98° C. for 35 min.

In one embodiment of the method, the herbal pharmaceutical composition containing a water-soluble extract as active ingredient.

This invention will be better understood by reference to the Experimental Details which follow, but those skilled in the art will readily appreciate that the specific experiments detailed are only illustrative of the invention as described more fully in the claims which follow thereafter.

EXAMPLES

The examples below are non-limiting and are merely representative of various aspects and features of the present invention.

Example 1

Material and Methods

DCB-SLE1 Preparation and Optimal Dose Selection

The extraction was performed by mixing with equal amount of each herb to a total of 1500 grams soaking in 15 L ddH$_2$O for 1 hr and then boiled at 98° C. for 35 min following by filtration with No. 400 mesh filter. The extraction was done for twice. Two filtrates were combined and evaporated to powder (DCB-SLE1).

Based on the guidance of IND regulations in the Republic of China Taiwan Food and Drug Administration, a 24-wk oral toxicity study in BALB/c mice was performed for evaluation of the safety of DCB-SLE1 that was used in the present study. The results showed that no abnormality in appearance and in body weight and no observable pathological changes were found in the major organs of any BALB/c mice between any the study groups. Besides, in a 13-wk subchronic oral toxicity study, DCB-SLE1 showed that no ocular finding was attributed to the administration of DCB-SLE1 in Sprague-Dawley rats, and no significant difference in all hematology parameters between DCB-SLE1-treated rats and untreated normal control rats. All animals survived through the entire study period, and no difference was shown in the change in body weight at weekly intervals among DCB-SLE1 and untreated normal control groups during the 13-wk dosing period. In the preliminary study, after three consecutive 6-wk treatment courses (different dose groups) with a 2-wk interval, the dose of 12.5 g/kg body wt of DCB-SLE1 can ameliorate nephritis, including proteinuria, hematuria, and renal function, and mortality in a spontaneously occurring lupus nephritis model in NZB/W F1 mice (not administered with LPS). Therefore, DCB-SLE1 at 12.5 g/kg body weight was used to treat the animals in the subsequent experiments.

Establishment of the ASLN Model and Experimental Protocol

An LPS-induced ASLN mouse model was established in the 8-week-old female NZB/W F1 mice by twice weekly intraperitoneal injection of LPS (Sigma, Mo., USA) as described (*Rheumatology (Oxford)*, 46: 1277-1284, 2007). Two days after first dose of LPS for the ASLN induction, the mice were divided into two groups of 6 mice each and daily administrated with DCB-SLE1 or vehicle (normal saline) via oral gavage till mice sacrificed. The age-matched NZB/W F1 mice that were injected with normal saline were used as normal controls (*Rheumatology (Oxford)*, 46: 1277-1284, 2007). All mice were killed at week 1 or week 5 after disease induction. The tissue specimens of spleen, renal cortical tissue, blood, and urine were collected at the indicated times and stored appropriately before analysis. All animal experiments were performed with the ethical approval of the Institutional Animal Care and Use Committee of The National Defense Medical Center, Taiwan and performed according to the ethical rules in NIH Guide for the Care and Use of Laboratory Animals.

Clinical and Pathologic Evaluation

The urine samples were collected in metabolic cages weekly, and urine protein were determined, and urine blood were determined by Urine Test Strip (Siemens, Tokyo, Japan). Serum samples were collected at mice sacrificed to measure serum levels of blood urea nitrogen (BUN) and creatinine (Cr). The examination of renal pathology and scoring were performed in a blinded fashion by a pathologist, and the severity of renal lesions was scored. The percentage of glomeruli showing proliferation, neutrophil infiltration, crescent formation, fibrinoid necrosis, and periglomerular inflammation was calculated from 50 randomly sampled glomeruli.

IF, IHC, and Detection of Apoptosis

For immune complex detection, frozen renal tissues were prepared and then stained with FITC-conjugated goat antibodies against mouse IgG, IgM, or C3 (Cappel, N.C., USA). Fifty glomeruli were examined on each slide and assigned values of staining intensity from 0 to ≥3. The total intensity score was calculated according to the following equation for each specimen: total intensity score=(% glomeruli intensity negative×0)+(% glomeruli intensity trace intensity×0.5)+(% glomeruli 1+intensity×1)+(% glomeruli 2+intensity×2)+(% glomeruli 3+intensity×3). The values ranged from 0 to a maximum of 300.

For immunohistochemistry (IHC), formalin-fixed and paraffin-embedded renal sections were prepared as described (*J Am Soc Nephrol*, 18: 2473-2485, 2007), and primary antibodies against mouse CD3 (pan-T cell; Serotec), CD4 (T helper cell; BioLegend, CA, USA), F4/80 (monocytes/macrophages; Serotec, N.C., USA), CD11b (macrophages/neutrophils; BD Biosciences), monocyte chemoattractant protein 1 (MCP-1; Santa Cruz Biotechnology, Santa Cruz, Calif.), IL-6 (R&D Systems, Minneapolis, Minn.), or NF-κB p65 (Cell Signaling Technology, MA, USA) were used, respectively, and then secondary biotinylated antibodies (Dako, Glostrup, Denmark) and avidin-biotin-peroxidase complex (Dako). For studying CD8, frozen sections were fixed in acetone for 5 min and stained with primary antibodies against mouse CD8 (T cytotoxic cell, BD Biosciences). The Alexa Fluor 594-conjugated secondary antibody (Invitrogen, Carlsbad, Calif.) was then applied to the sections. The isotypematched IgG from the same species of the primary antibodies was used as an antibody control for IHC staining. Semiquantitative evaluations for staining were performed as described (*J Am Soc Nephrol*, 18: 2473-2485, 2007).

For the detection of apoptosis, TUNEL assay was performed. Paraffin-embedded sections were stained with an ApopTag Plus Peroxidase in Situ Apoptosis Detection kit (Chemicon, Calif., USA) according to the manufacturer's instructions and the number of apoptotic cells in the glomerulus counted as the number of TUNEL-positive cells per glomerular cross-section (gcs) as described (*J Am Soc Nephrol*, 18: 2473-2485, 2007).

Analyses of T/B Cell Activation, T Cell Proliferation, and NK Cell Activity

Mice splenocytes isolation was performed as described (*J Am Soc Nephrol*, 18: 2473-2485, 2007) for T or B cell activation, T cell proliferation, or NK cell activity analysis. Isolated cells were stained with FITC-conjugated anti-mouse CD3 (17A2), CD4 (G11.5), or CD19 (B cell, 1D3) antibodies and phycoerythrin-conjugated anti-mouse CD69 (H1.2F3) antibodies (all from BD Biosciences, CA, USA) for T or B cell activation with FACSCalibur (BD Biosciences) as described (*J Am Soc Nephrol*, 18: 2473-2485, 2007).

T-cell proliferation of splenocytes was examined by $^3$H-methyl thymidine (Amersham Pharmacia Biotech, NJ, USA) uptake and the incorporated $^3$H-methyl thymidine was measured using a TopCount (Packard, PerkinElmer, MA, USA) as described (*J Am Soc Nephrol*, 18: 2473-2485, 2007). All assessments of proliferative responses were carried out in at least triplicates.

NK cell activity was determined using the LIVE/DEAD Cell-Mediated Cytotoxicity kit (Molecular Probes, USA) as described (*Evid Based Complement Alternat Med*, 7: 189-195, 2008). In brief, $1 \times 10^5$ target cells (YAC-1 cells from a murine lymphoma) were pre-labeled with 1 µl 3 mM DiOC18 fluorescent dye for 0.5 h, and excess dye was removed by washing with PBS. Then the labeled YAC-1 cells were co-incubated with $2 \times 10^6$ splenocytes for 4 h, and 100 µL of 3.75 mM propidium iodine dye was added to the reaction at 4° C. for 20 min avoiding the light. NK cell activity was analyzed by flow cytometry and was calculated with the equation: NK activity (%)=viability of treated group (%)−viability of blank group (%).

Measurement of Serum Autoantibody Levels

The serum levels of anti-double stranded DNA (dsDNA) antibody (Alpha Diagnostic) was measured with an ELISA reader (BioTek) at a wavelength of 450 nm using commercial ELISA kits according to the manufacturer's instructions.

IL-6, IL-17A, and IL-18 mRNA Examination

Renal cortex RNA was extracted using TRIzol reagent (Invitrogen, CA, USA) according to the manufacturer's instructions and real-time RT-PCR was used to verify IL-6, IL-17A or IL-18 gene expression. The primers used were: IL-6: 5'ATGAAGTTCCTCTCTGCAAGAGACT3', 5'CACTAGGTTTGCCGAGTAGATCTC3'; IL-17A: 5'-TCCAC-CGCAATGAAGACCCTGATA-3', 5'-ACCAGCATCT-TCTCGACCCTGAAA-3; IL-18: 5'-ACTGTACAACCGGAGTAATACGG-3', 5'-TCCATCT-TGTTGTGTCCTGG-3; GAPDH: 5'-TCCGCCCCTTCT-GCCGATG-3', 5'-ACGGAAGGCCATGCCAGTGA-3'. Real-time quantification was performed using the BIO-RAD iCycler iQ system (BioRad) according to manufacturer instructions. Amplifications were normalized to GAPDH using the $2^{-\Delta CT}$ method.

Measurement of Serum Inflammatory Cytokine Levels

The concentration of IL-6, IL-10, MCP-1, IFN-γ, TNF-α, and IL-12p70 in serum were determined by using the BD Cytometric Bead Array Mouse Inflammation kit (BD Biosciences) according to the manufacturer's protocol. Flow cytometry analysis was carried out using a FACSCalibur (BD Biosciences). Serum levels of IL-17 (R&D Systems) and IL-18 (MBL, Aichi, Japan) were measured using commercial ELISA kits according to the manufacturer's instructions.

Renal NF-κB Activity Detection

The nuclear NF-κB activity was quantified using an ELISA-based TransAM NFκB kit (Active Motif, Tokyo, Japan) according to manufacturer's protocol. The nuclear protein of renal tissues was extracted using the Nuclear Extract Kit (Active Motif) according to the manufacturer's instructions. The NF-κB activity was determined by reading the absorbance on an ELISA plate reader (Bio-Tek) at 450 nm with a reference wavelength of 655 nm.

Data Analysis

The results are presented as the mean±SEM. Comparisons between two groups were performed using Student's t test. A p value<0.05 was considered statistically significant.

Example 2

DCB-SLE1 Reduces Proteinuria, Hematuria, Renal Function Defects, and Severe Renal Lesions in the ASLN Model Untreated ASLN mice showed increased urine protein levels starting at week 2 after ASLN induction, and these continued to rise until the mice were euthanized at week 5 (FIG. 1A); the mice also showed gross hematuria (dipstick test 3+) from week 4 to week 5 (FIG. 1B). These effects were significantly inhibited in the DCB-SLE1-treated ASLN (ASLN+DCB-SLE1) mice, although they still showed mild proteinuria compared with normal controls. The untreated ASLN mice also showed significantly increased serum levels of blood urea nitrogen (BUN) (FIG. 1C) and creatinine (Cr) (FIG. 1D) at week 5, and again there was a dramatic improvement in renal function in the ASLN+DCB-SLE1 mice. At week 1, there was no significant difference in levels of BUN or Cr among the normal control, untreated ASLN mice, and ASLN+DCB-SLE1 mice.

As shown in FIG. 1E, at week 5 renal histopathology of the untreated ASLN mice revealed the characteristic severe lesions of 1) neutrophil infiltration and florid crescent formation (both cellular and fibrous types) in the glomeruli; and 2) interstitial inflammation, featuring striking periglomerular mononuclear leukocyte infiltration and tubular atrophy associated with protein casts. Fibrinoid necrosis of the tuft area was also seen in some of the affected glomeruli. In contrast, all of these renal lesions were substantially reduced by DCB-SLE1 treatment, although the mice still showed mild glomerular proliferation. At week 1, there were no obvious pathological changes in the kidney in either untreated ASLN or ASLN+DCB-SLE1 mice.

The body weight of mice was recorded every week. The growth (percent increase in body weight compared with the initial body weight) of ASLN+DCB-SLE1 mice was no different from that of normal controls (ASLN+DCB-SLE1 mice, 10.8% vs. normal controls, 11.1%), whereas the growth of untreated ASLN mice was significantly inhibited (only a 1.9% increase) at week 5. The increase in body weight of the ASLN+DCB-SLE1 mice reflected the improved condition of these mice, suggesting that DCB-SLE1 might improve the symptoms of cachexia of ASLN mice. In addition, all mice treated with DCB-SLE1 showed normal activity and no evidence of hair loss or appetite change, compared with the ill looking untreated ASLN mice, with a poor coat and loss of appetite.

Example 3

DCB-SLE1 Reduces Autoantibody in Serum and Immune Deposits in the Kidney

Figure 2:
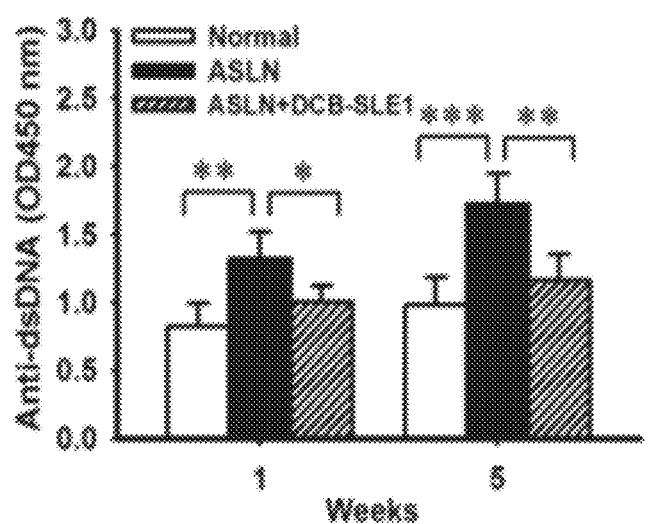
FIG. 2 shows the autoantibodies and complement components in serum and immune complex deposition in the kidney. (A) anti-dsDNA antibody levels. (B) antinuclear antibody (ANA). (C)-(D): serum levels of C3 (C) and C4 (D). (E)-(G): detection of IgG (E), IgM (F), and C3 (G) deposits in the glomeruli. Original magnification, 400×. The semiquantitative analysis is shown on the right. Each bar represents the mean±SEM for six mice per group. *$p<0.05$, $p<0.01$, *$p<0.005$.
Figure 2:
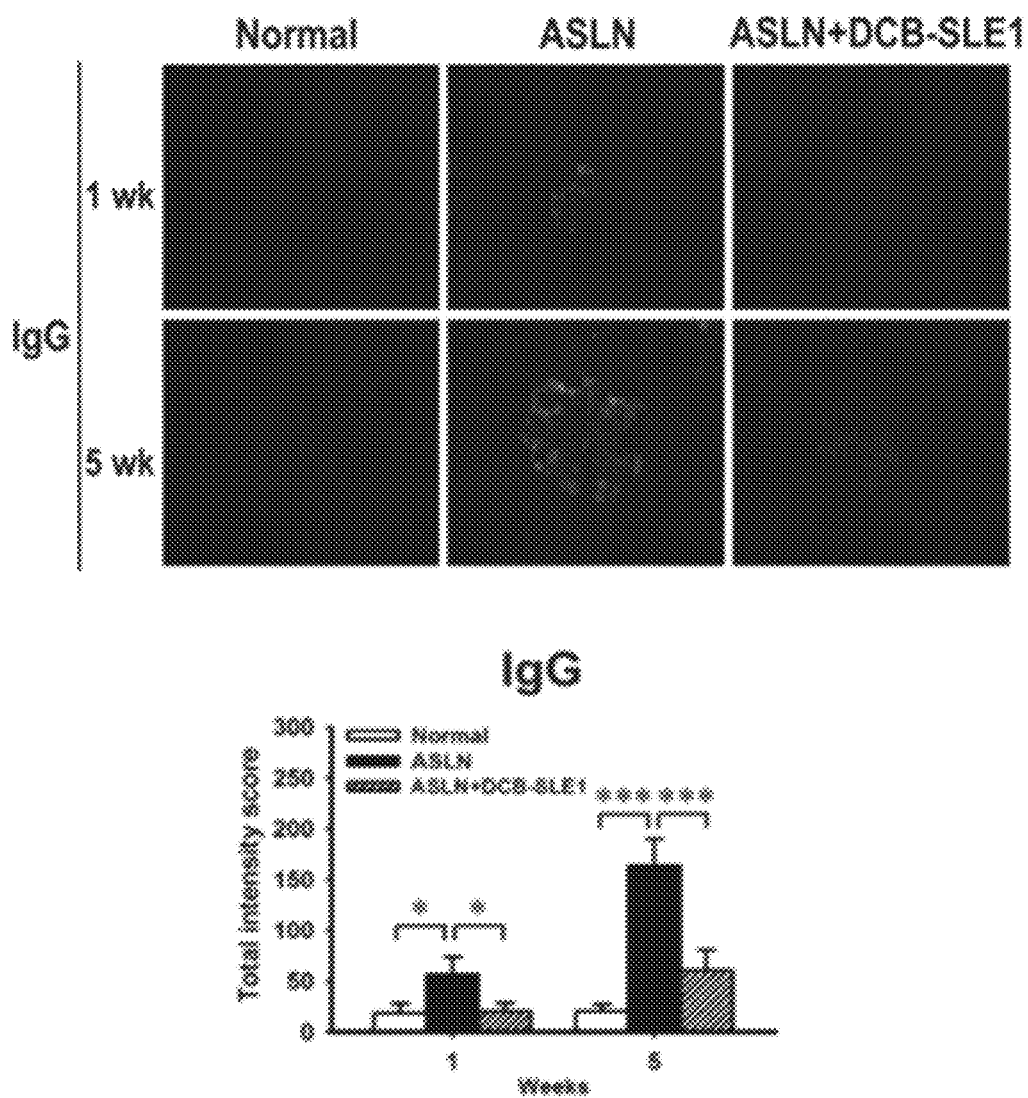
Figure 2:
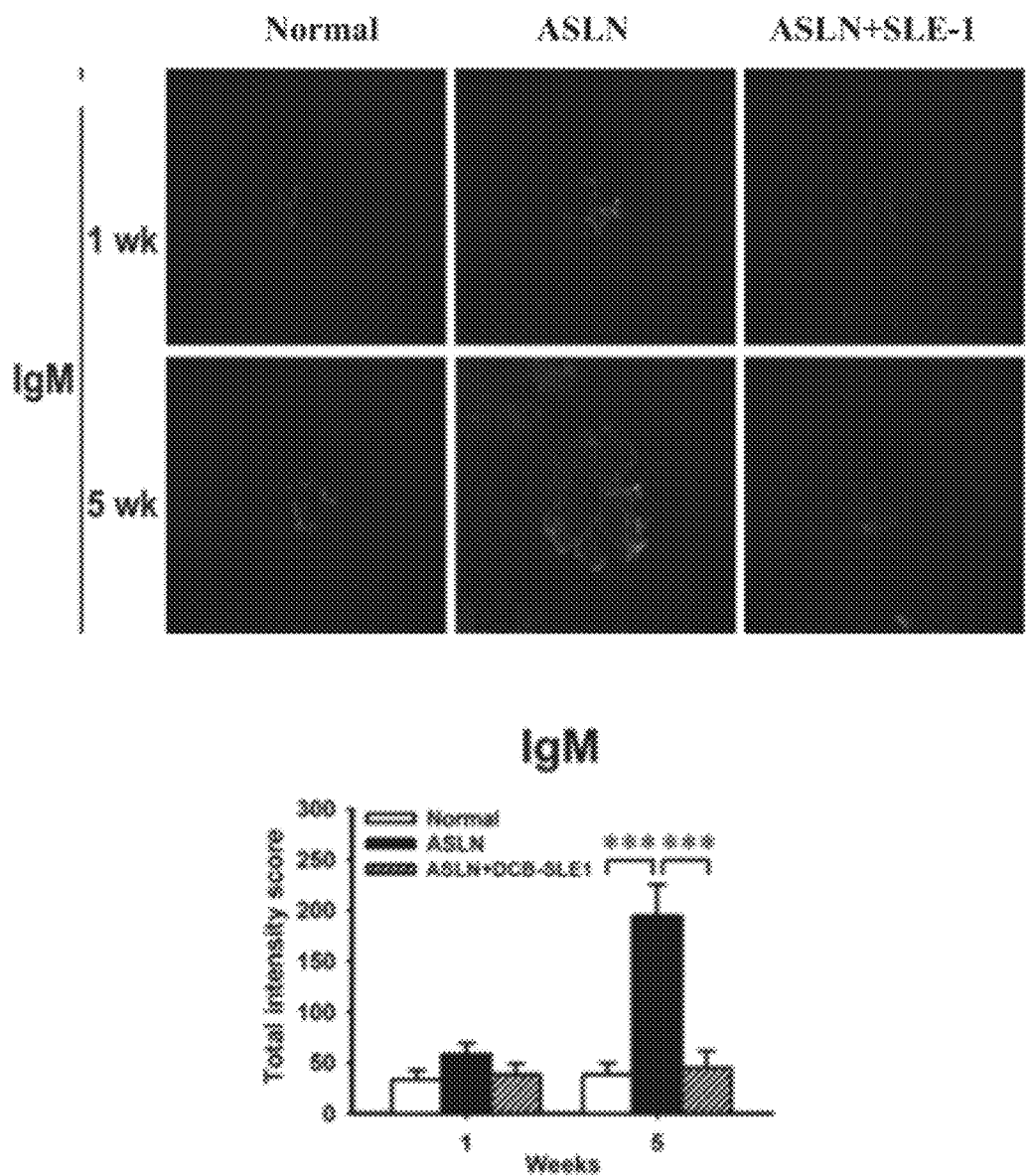
Figure 2:
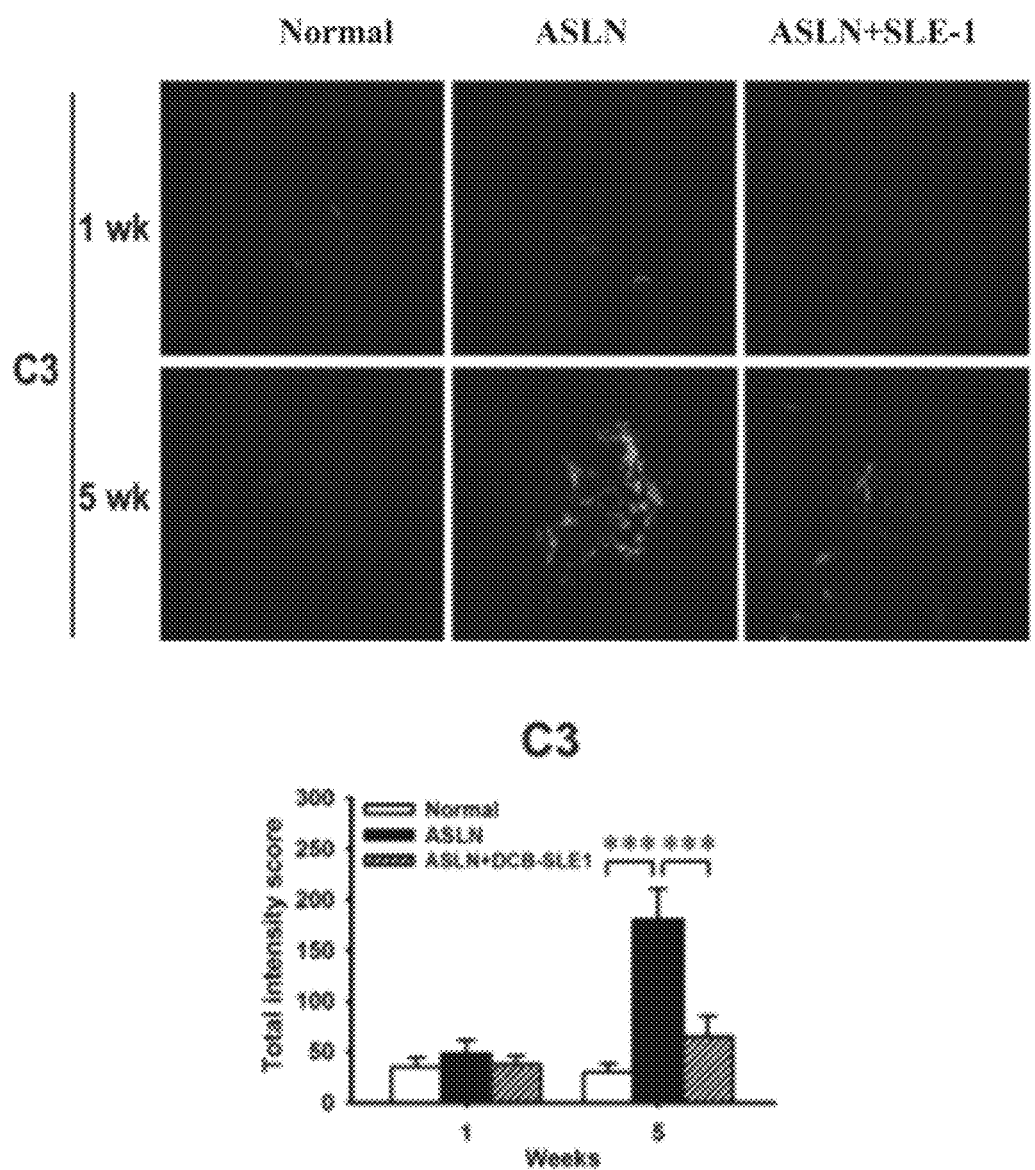

Since autoantibody-induced immune complex deposition in the kidneys is considered to be the primary cause of lupus nephritis (*Curr Opin Rheumatol*, 21: 489-494, 2009; *J Clin Invest*, 45: 1732-1740, 1966; *J Immunol*, 168: 3072-3078, 2002). As shown in FIG. 2A, serum anti-dsDNA autoantibody levels in untreated ASLN mice showed a significant increase as early as week 1 and a further increase at week 5 compared with normal controls but were significantly reduced in ASLN+DCB-SLE1 mice at both weeks 1 and 5. In parallel, as shown in FIG. 2B, although the serum from untreated ASLN mice gave a strong staining pattern at week 5, and a weaker pattern of staining at week 1, compared with the negative staining in normal control sera, the serum from ASLN+DCB-SLE1 mice generated a weak pattern of staining at week 5, and negative staining at week 1. As shown in FIG. 2C, untreated ASLN and ASLN+DCB-SLE1 mice showed no significant difference in serum C3 levels compared with normal controls at week 1. However, there was significant reduction in serum C3 levels in untreated ASLN mice at week 5 compared with normal controls, but this effect was suppressed by administration of DCB-SLE1 in ASLN+ DCB-SLE1 mice. There was no significant difference in serum C4 levels (FIG. 2D) among the normal controls, untreated ASLN, and ASLN+DCB-SLE1 mice.

Furthermore, at week 1 untreated ASLN mice showed a significant increase in IgG deposition in the glomerulus (FIG. 2E) and a slight but not significant increase in deposition of IgM (FIG. 2F) and C3 (FIG. 2G), with a much greater increase in all three at week 5. All of these effects were significantly reduced by DCB-SLE1 administration at both weeks 1 and 5.

Example 4

Figure 3:
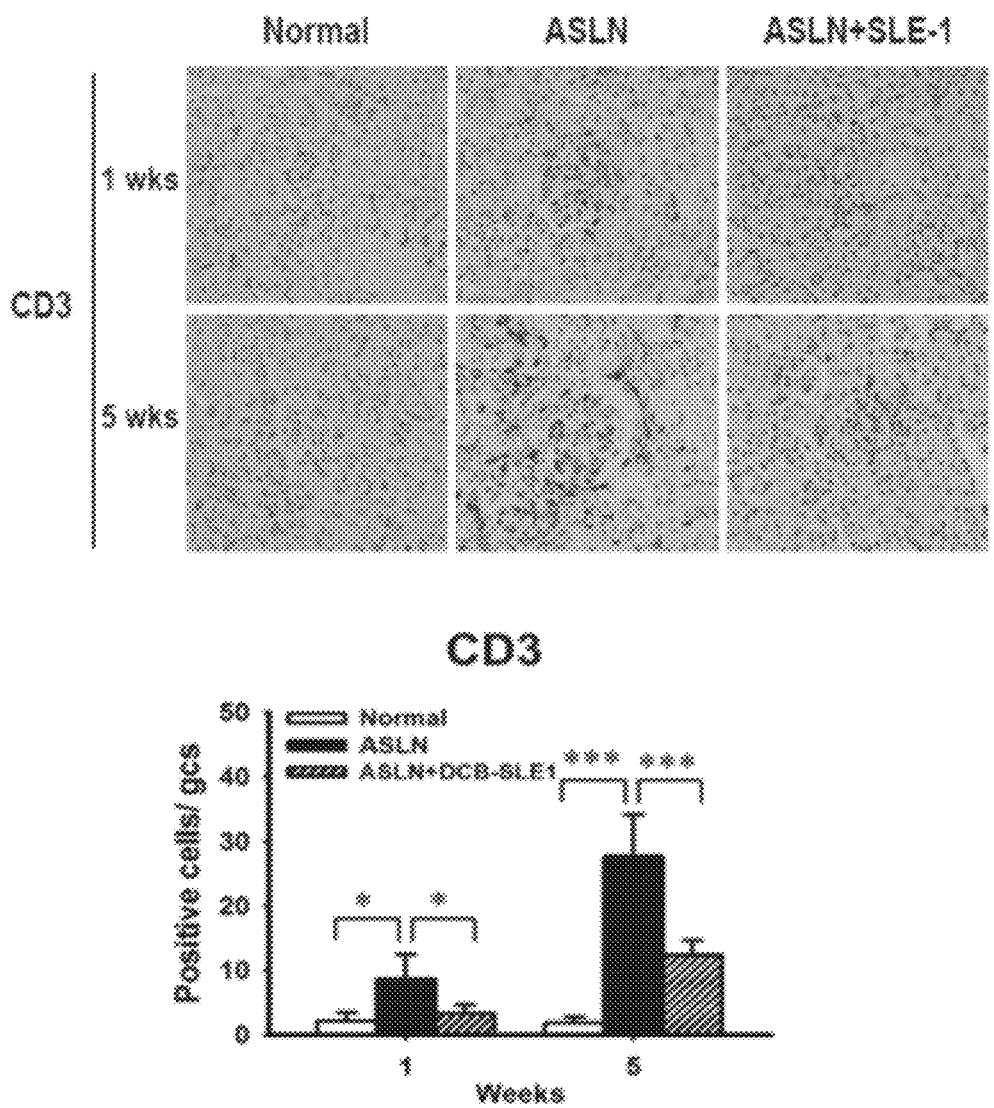
FIG. 3 shows the T cell and monocyte/macrophage infiltration in the kidney. Detection of CD3$^+$ T cell (A), CD4$^+$ T cell (B), CD8$^+$ T cell (C), F4/80 monocytes/macrophages (D), and CD11b neutrophils (E) by immunohistochemical staining. Original magnification, 400×. Semiquantification scoring of CD3$^+$ T cell (B), CD4$^+$ T cell (D), or F4/80 monocytes/macrophages (F). The semiquantitative analysis is shown at the bottom right. Data are mean±SEM for six mice per group. *p<0.05, p<0.01, *p<0.005, #Not detectable.
Figure 3:
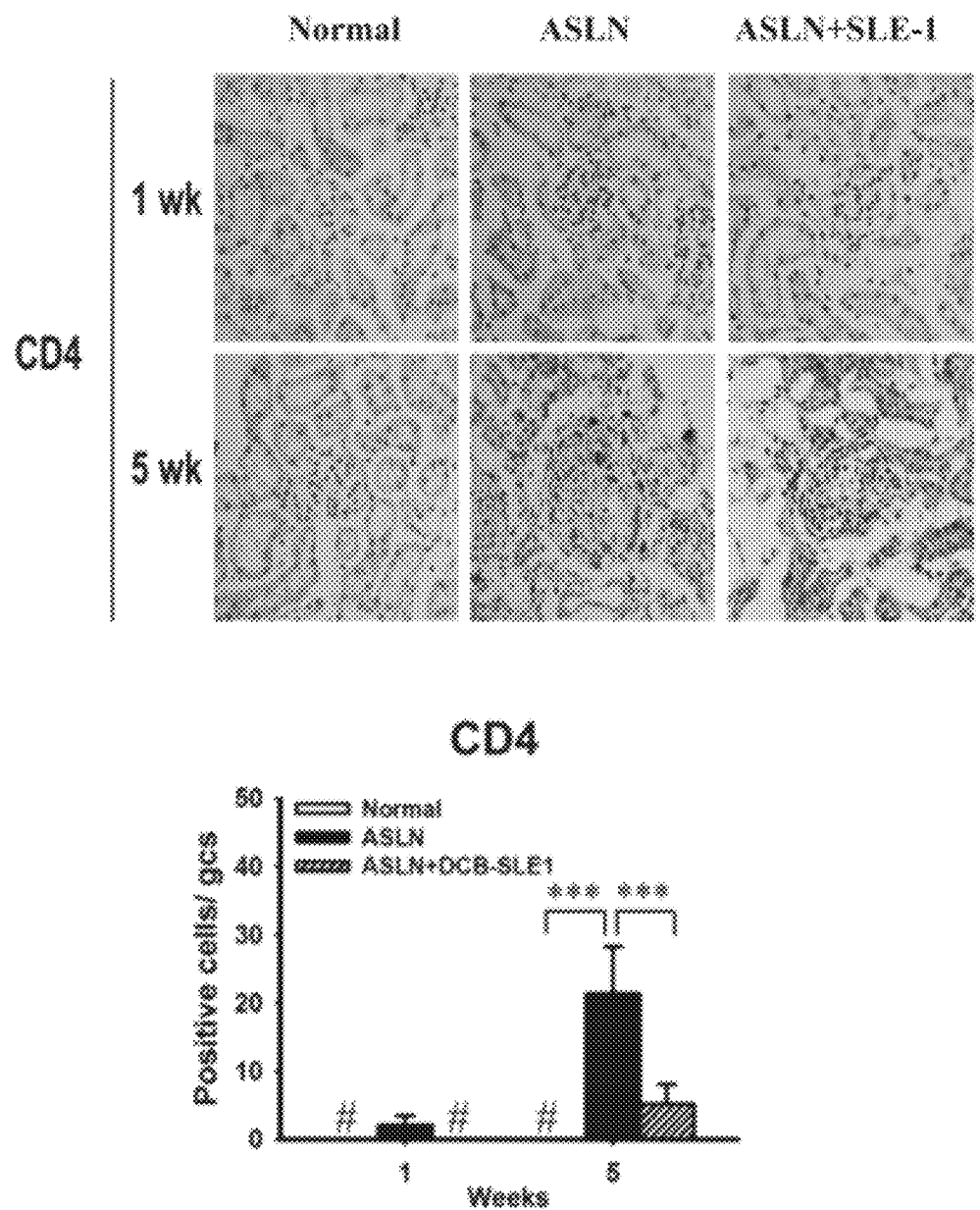
Figure 3:
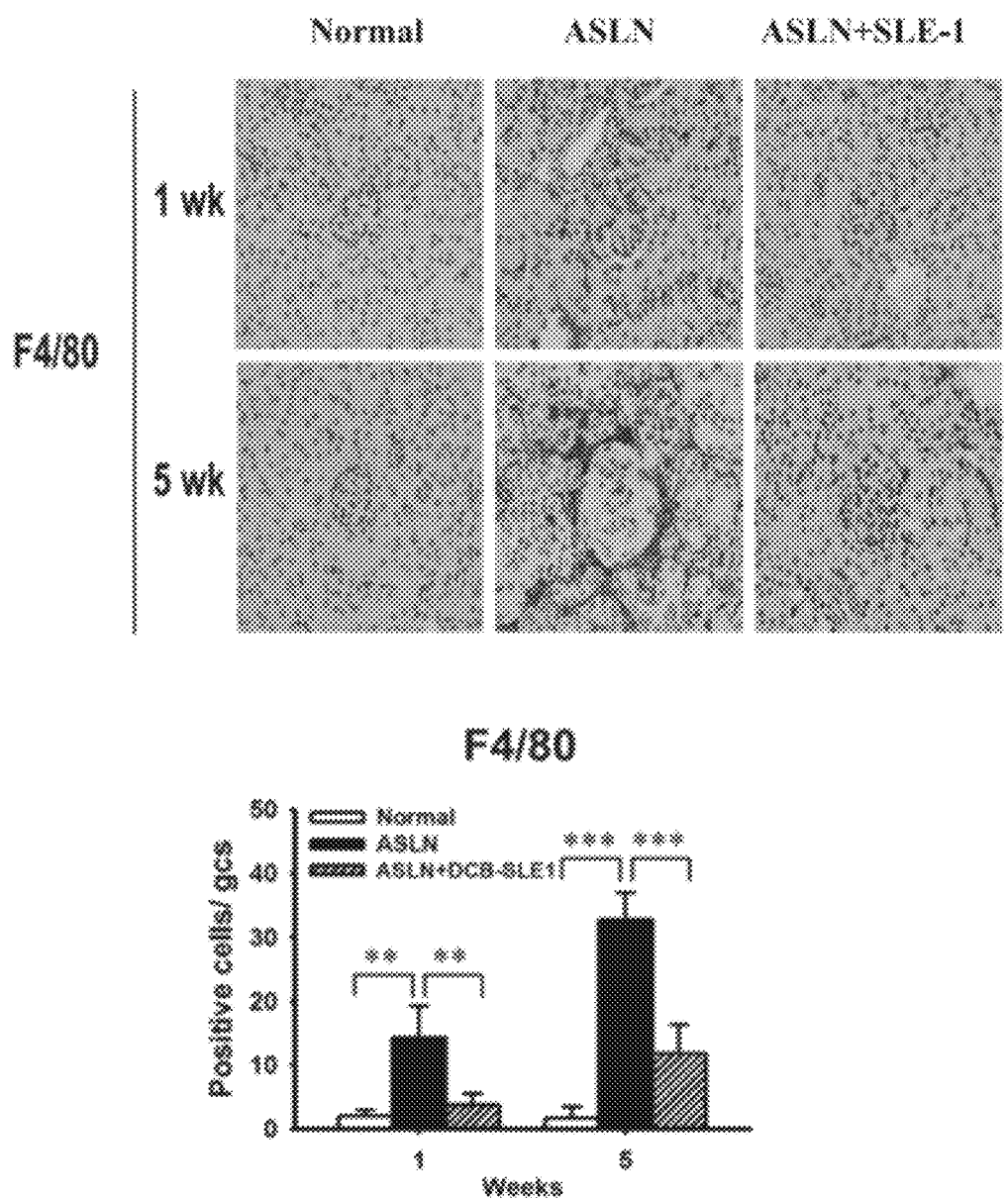
Figure 3:
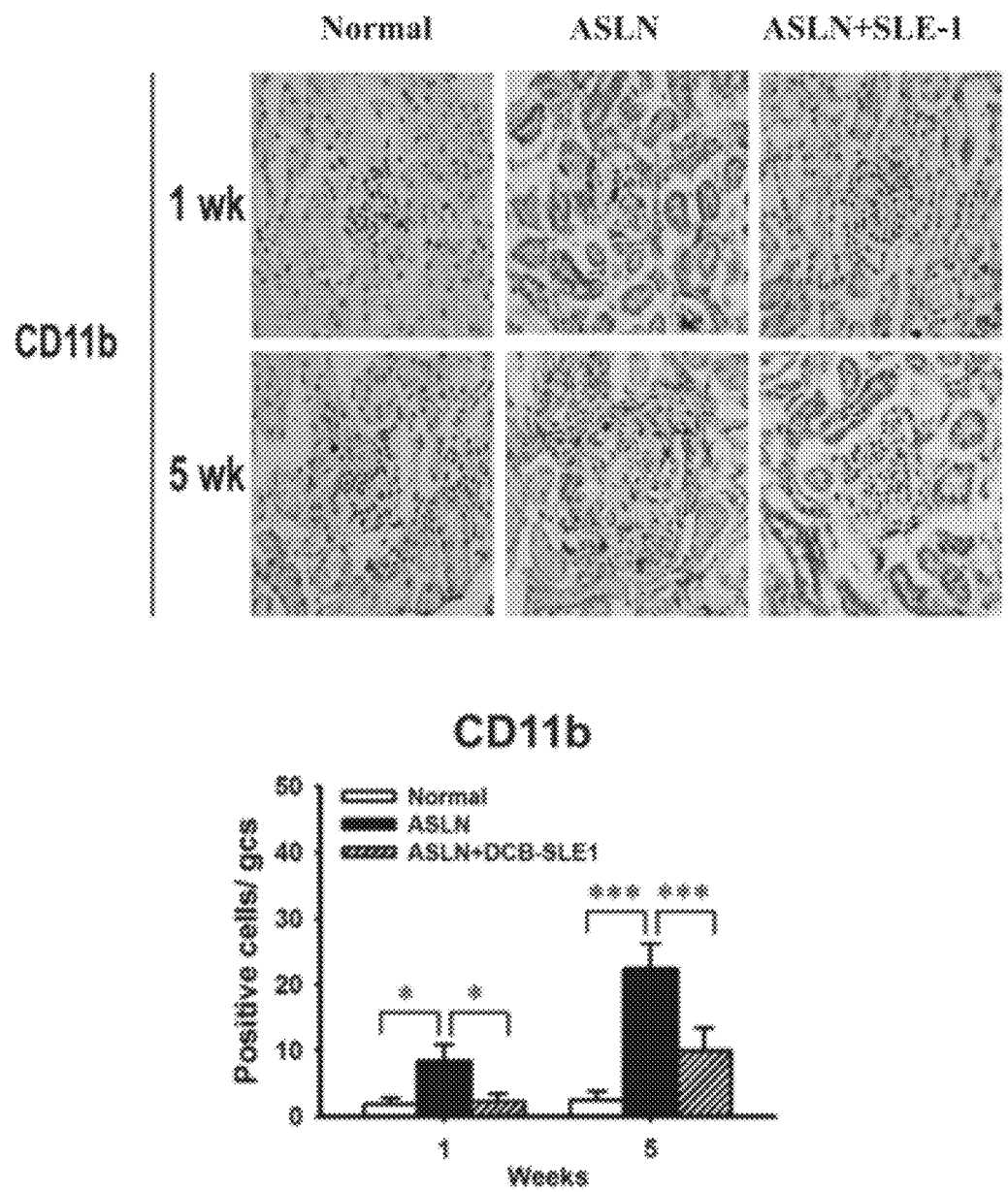

DCB-SLE1 Inhibits Renal Filtration of T Cells, Monocytes/Macrophages, and Neutrophils Cellular immune effectors, such as T cells, macrophages, and neutrophils, play an important role in rapidly progressive glomerular nephritis. T cells, which infiltrate the kidney and either cause direct cytotoxicity or recruit other inflammatory cells, such as monocytes/macrophages, play a crucial role in the pathogenesis of experimental and human lupus nephritis (*Curr Opin Rheumatol*, 16: 548-552, 2004; *J Biomed Biotechnol*, 2010: 457146, 2010). This study examined whether intrarenal infiltration of T cells, monocytes/macrophages, and neutrophils was suppressed by DCB-SLE1 administration. IHC studies at week 5 showed diffuse infiltration of T cells ($CD3^+$, $CD4^+$, and $CD8^+$; FIG. 3A-C), monocytes/macrophages ($F4/80^+$; FIG. 3D), and neutrophils ($CD11b^+$; FIG. 3E) into the periglomerular region of the renal interstitium in untreated ASLN mice, and these effects were significantly reduced by administration of DCB-SLE1 (all $p<0.005$). At week 1, DCB-SLE1 administration caused a significant decrease in the infiltration of $CD3^+$, $F4/80^+$, and $CD11b^+$ cells, and only a few, or no $CD4^+$ and $CD8^+$ cells were seen in either untreated ASLN mice or ASLN$^1$ DCBSLE1 mice.

Example 5

DCB-SLE1 Decreases IL-6, IL-17A, and IL-18 mRNA Expression in Kidney

Figure 4:
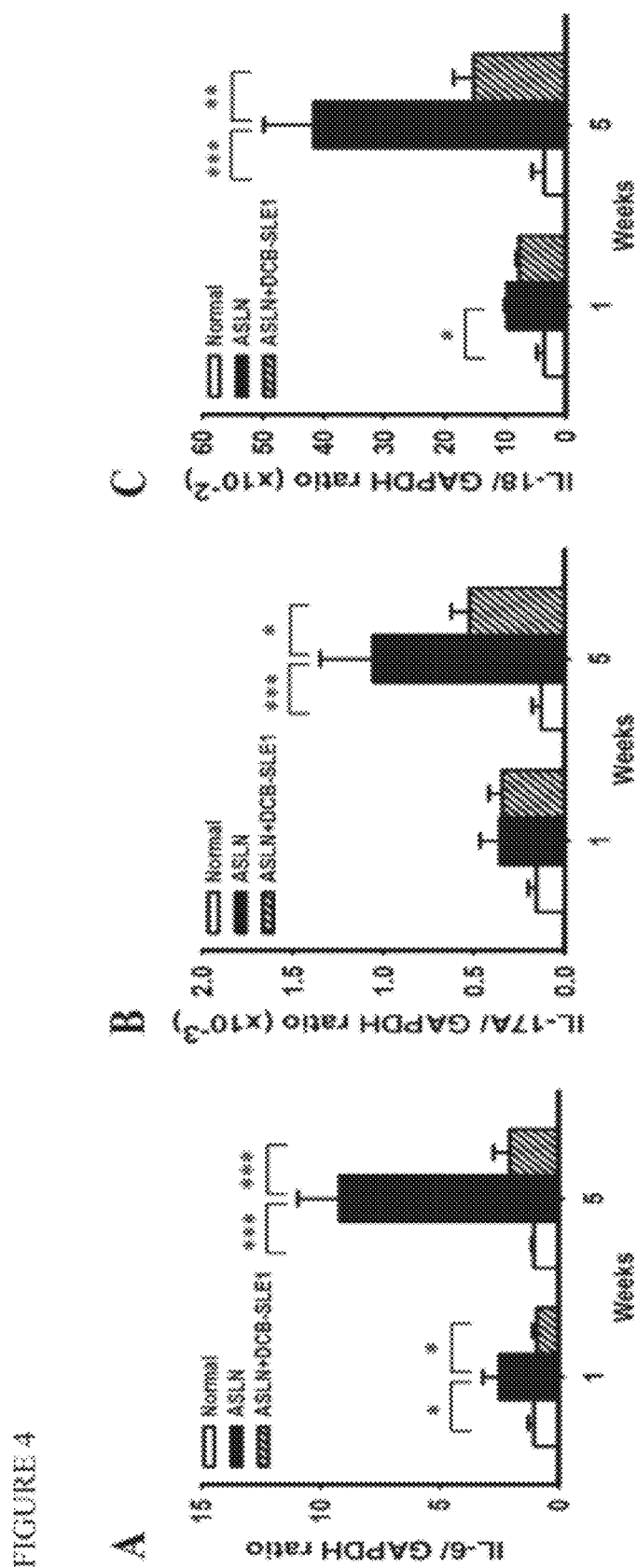
FIG. 4 shows that DCB-SLE1 inhibits renal IL-6, IL-17A, and IL-18 mRNA expression. Detection of IL-6 (A), IL-17A (B), or IL-18 (C) mRNA expression by real time RT-PCR. Data are mean±SEM for six mice per group. *p<0.05, p<0.01, *p<0.005.

IL-17, secretion by Th17 cells, is a cytokine with powerful inflammatory properties (*J Biomed Biotechnol*, 2010: 943254), and an enhanced Th17 cell response, seen as IL-6 overproduction, has been implicated in disease activity in patients with lupus nephritis (*Chin Med J (Engl)*, 116: 543-548, 2003; *J Rheumatol*, 37: 2046-52, 2010; *Arthritis Res Ther*, 12: R53, 2010). The effects of DCB-SLE1 on renal mRNA expression levels of IL-6 and IL-17A in the ASLN model were further determined by real time reverse transcription (RT)-PCR. At week 1, IL-6 mRNA levels in the kidney were significantly lower in ASLN+DCB-SLE1 mice than in untreated ASLN mice (FIG. 4A, $P<0.05$), but there was no significant difference in IL-17A mRNA levels between the two groups (FIG. 4B). However, at week 5 a significant decrease in kidney levels of both mRNAs was seen in ASLN+ DCB-SLE1 mice compared with untreated ASLN mice (FIG. 4, A and B, both $P<0.005$).

IL-18 is involved in promoting the migration of circulating dendritic cells toward the kidney in active lupus nephritis (*J Biomed Biotechnol*, 2010: 457146, 2010). This study measured IL-18 mRNA levels in the kidney. As shown in FIG. 4C, the real-time RT-PCR showed a significantly increase in renal IL-18 mRNA levels as early as week 1 in untreated ASLN mice compared with normal controls ($p<0.05$) and an even greater increase at week 5 ($p<0.005$), and this large increase at week 5 was significantly inhibited in the ASLN+DCB-SLE1 mice ($p<0.01$), with a slight difference at week 1.

Example 6

Figure 5:
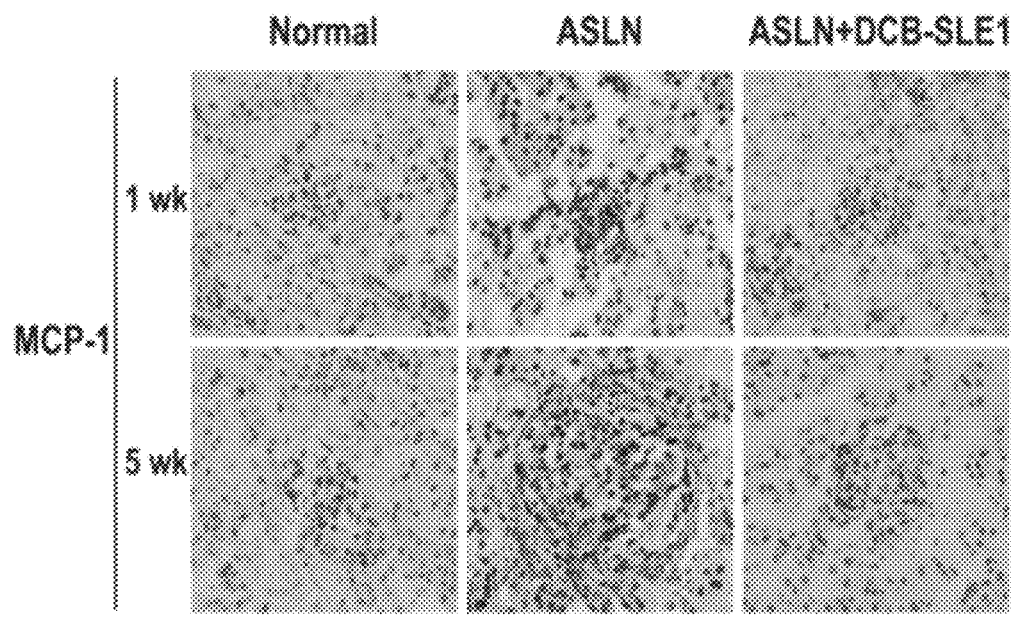
FIG. 5 shows that DCB-SLE1 inhibit the intra-renal MCP-1 and IL-6 production. Detection of MCP-1 (A) or IL-6 (B) by immunohistochemistry staining. Original magnification, 400×. Semiquantification scoring is shown in right panel. Data are mean±SEM for six mice per group. *p<0.05, ***p<0.005.
Figure 5:
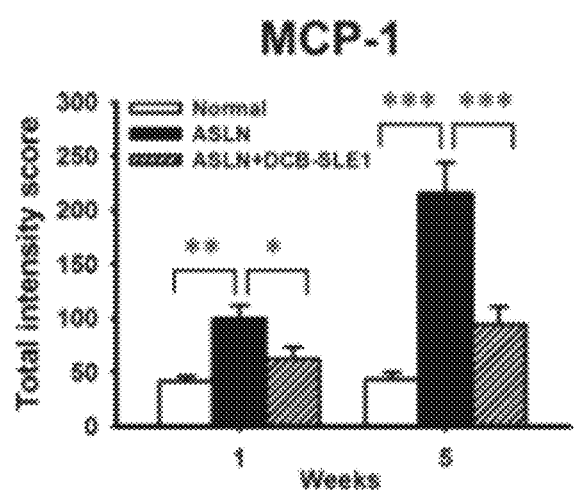
Figure 5:
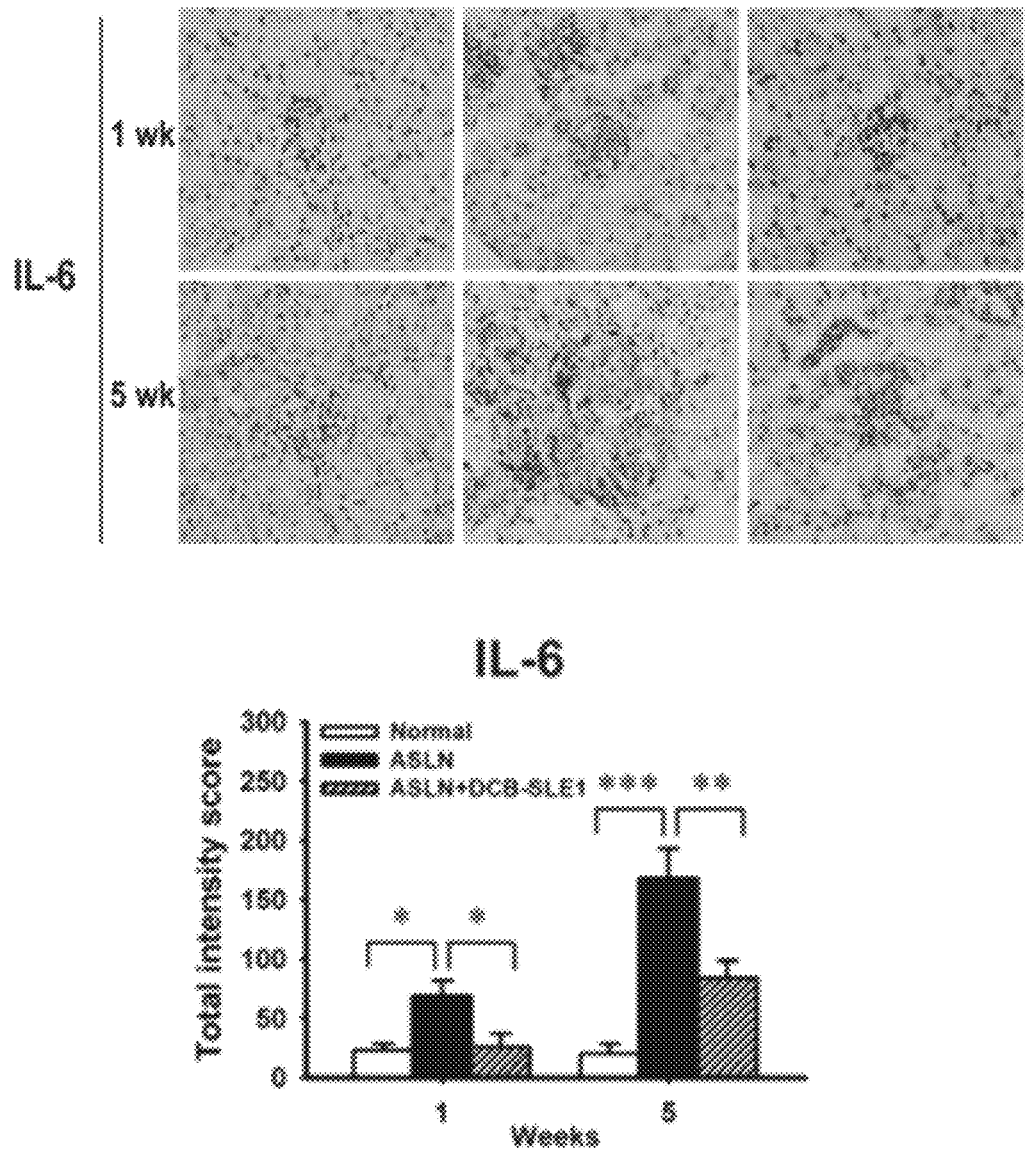

DCB-SLE1 Inhibits Renal IL-6 and MCP-1 Protein Expression and NF-κB Activation IL-17 has been reported to recruit neutrophils and macrophages to inflammation sites by inducing overexpression of MCP-1 (*J Biomed Biotechnol*, 2010: 943254). This study analyzed protein expression of these cytokines in the kidney by IHC and found that expression of MCP-1 (FIG. 5A) and IL-6 (FIG. 5B) was significantly increased at week 1 in untreated ASLN mice compared with normal controls (MCP-1, $p<0.01$; IL-6, $p<0.05$) and progressively increased at week 5 (both $p<0.005$). In contrast, ASLN+DCB-SLE1 mice showed significantly reduced renal expression of these cytokines compared with untreated ASLN mice at both weeks 1 (both $p<0.05$) and 5 (MCP-1, $p<0.005$; IL-6, $p<0.01$).

Figure 6:
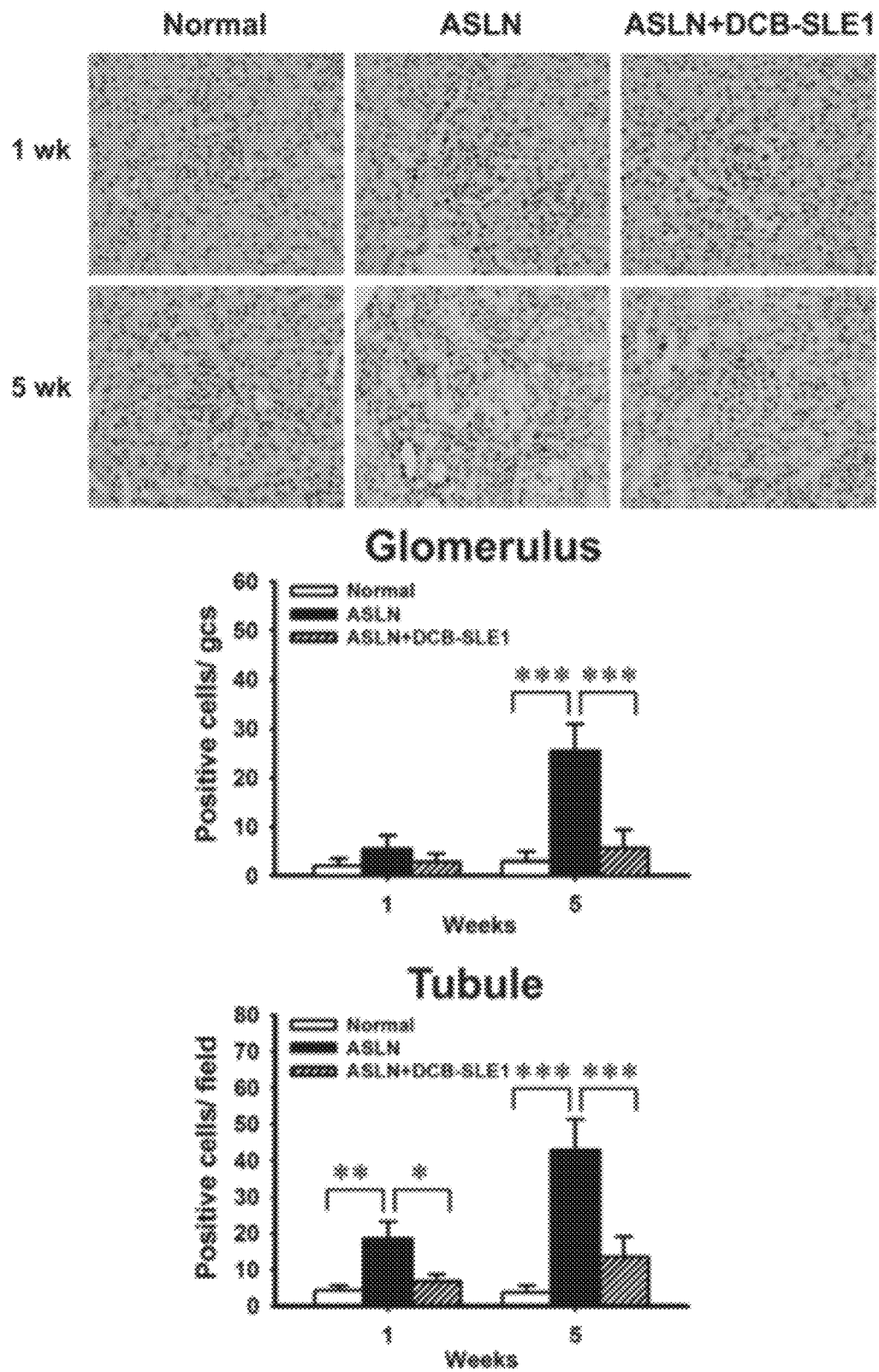
FIG. 6 shows that DCB-SLE1 suppresses renal NF-κB activity. (A) Detection of NF-κB p65 by immunohistochemistry staining. Original magnification, 400×. Semiquantification scoring of glomerulus and tubule is shown in right panel. (B) Detection kidney NκFB activity by ELISA-based TransAM NFκB kit. Data are mean±SEM for six mice per group. *p<0.05, ***p<0.005.
Figure 6:
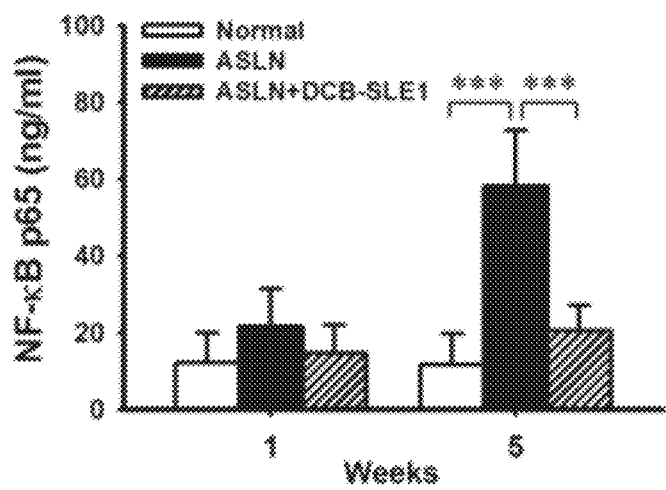

This study measured NF-κB activation, since these results in expression of genes that encode these proteins (*Immunol Rev*, 127: 25-50, 1992; *Mol Med*, 4: 413-424, 1998). As demonstrated by IHC in FIG. 6A, untreated ASLN mice showed significantly increased NF-κB p65 activity in the kidney compared with normal controls, as shown by its nuclear location in the glomeruli and tubulointerstitium and in mononuclear cells infiltrating the periglomerular regions, and DCB-SLE1 administration caused a significant decrease in NF-κB activation at both weeks 1 and 5 (both $p<0.005$). Moreover, an ELISA based NF-κB p65 activation assay demonstrated the similar pattern, although there was no significant difference among normal control, untreated ASLN, and ASLN+DCB-SLE1 mice at week 1 (FIG. 6B).

Example 7

DCB-SLE1 Decreases Serum Levels of Inflammatory Cytokines

This study further investigated whether DCB-SLE1 administration reduced systemic inflammation, as represented by serum levels of the inflammatory cytokines IL-6, MCP-1, IL-12p70, IFN-γ, TFN-α, IL-10, IL-17, and IL-18. Serum levels of IL-6 (FIG. 7A), MCP-1 (FIG. 7B), and IL-18 (FIG. 7G) were significantly increased in untreated ASLN mice compared with normal controls as early as week 1, and levels of all cytokines except IL-10 (FIG. 7F) progressively increased at week 5. In contrast, all of these effects were suppressed by administration of DCB-SLE1 in ASLN+DCB-SLE1 mice, with no significant difference in IL-10 levels. The serum levels of IL-17 were undetectable in all the mice.

Example 8

DCB-SLE1 Modulates Cellular Immune Responses

T and B cell abnormalities and the generation of pathogenic autoantibodies have been demonstrated to play an important role in the progression of lupus nephritis. The effects of DCB-SLE1 on systemic cellular immunity by using spleen tissues were examined.

Suppression of T/B Cell Activation

As shown in FIG. 8A and FIG. 8B, the percentage of $CD3^+CD69^+$ cells (activated T cells) in the spleen was significantly increased at both weeks 1 and 5 in untreated ASLN mice compared with normal controls (both $p<0.005$) and this effect was prevented by the DCB-SLE1 administration at both weeks 1 and 5 (week 1, $p<0.05$; week 5, $p<0.005$). Similarly, the percentage of $CD19^+CD69^+$ cells (activated B cells) in ASLN mice was significantly reduced by DCB-SLE1 administration to the same levels as those in normal controls at weeks 1 and 5 (FIG. 8C and FIG. 8D; week 1, $p<0.05$; week 5, $p<0.005$).

Inhibition of T Cell Proliferation

As shown in FIG. 8E, T cell proliferation in ASLN mice showed a dramatic increase at week 1, then tended to decrease at week 5, levels at both time points being significantly increased compared with those in normal control mice (both $p<0.005$), and DCB-SLE1 administration significantly reduced T cell proliferation to the levels seen in normal control mice at both weeks 1 and 5 (week 1, $p<0.005$; week 5, $p<0.01$).

Suppression of NK Cell Activity

NK cells play an important role in the development of lupus in NZB/W F1 mice because treatment with anti-NK1.1 monoclonal antibodies ameliorates the disease (*Immunology*, 125: 184-196, 2008). Therefore, the NK cells activity in spleen was further measured. Compared to normal control, the NK cells activity in disease ASLN mice was significantly increased at week 5. However, this effect was significantly inhibited by the administration of DCB-SLE1 to ACLN mice. There were no significant changes in the disease ASLN or DCB-SLE1 administrated ASLN mice compared with normal control mice at week 1 (FIG. 8F).

Example 9

DCB-SLE1 Prevents Apoptosis in the Spleen and Kidney

Abnormal regulation of apoptosis and accumulation of apoptotic cells have been reported to enhance the progression of lupus nephritis (*Am J Pathol*, 175: 97-106, 2009; *Rheumatology (Oxford)*, 42: 935-938, 2003), and marked apoptosis has been noted in the ASLN model (*Rheumatology (Oxford)*, 46: 1277-1284, 2007). This study tested whether DCB-SLE1 administration prevented apoptosis in the spleen or kidney in ASLN mice, using the TUNEL assay. Although apoptosis was seen in the spleen of untreated ASLN mice, it was significantly suppressed by DCB-SLE1 administration (FIG. 9A). In parallel, a significant reduction in apoptosis was observed in the glomeruli and some renal tubules of ASLN+SLE1 mice compared with untreated ASLN mice, although a few apoptotic figures were still seen in the renal tubules of ASLN¦SLE1 mice (FIG. 9B).

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. Modifications therein and other uses will occur to those skilled in the art. These modifications are encompassed within the spirit of the invention and are defined by the scope of the claims.

---

What is claimed is:

1. A method of treating a subject afflicted with nephritis, which comprises administering to the subject a herbal pharmaceutical composition comprising effective amounts of: Rhizoma *Atractylodis Macrocephalae*; *Eucommiae Cortex*; *Lonicerae Caulis*; and *Hedyotidis Diffusae* Herba.

2. The method of claim 1, wherein the herbal pharmaceutical composition reduces proteinuria, hematuria, renal function defects, and severe renal lesions in the subject.

3. The method of claim 1, wherein the herbal pharmaceutical composition reduces autoantibody in serum and immune deposits in the kidney of the subject.

4. The method of claim 1, wherein the herbal pharmaceutical composition inhibits renal infiltration of T cells, monocytes/macrophages, and neutrophils in the subject.

5. The method of claim 1, wherein the herbal pharmaceutical composition decreases IL-6, IL-17A, and IL-18 mRNA levels in the kidney of the subject.

6. The method of claim 1, wherein the herbal pharmaceutical composition inhibits renal IL-6 and MCP-1 protein expression and NF-κB activation in the subject.

7. The method of claim 1, wherein the herbal pharmaceutical composition decreases serum levels of inflammatory cytokines.

8. The method of claim 7, wherein the inflammatory cytokines are selected from the group consisting of IL-6, MCP-1, IL-12p70, IFN-γ, TNF-α, and IL-18.

9. The method of claim 1, wherein the herbal pharmaceutical composition modulates cellular immune responses in the subject.

10. The method of claim 1, wherein the herbal pharmaceutical composition is capable of inhibiting apoptosis in the kidney and spleen of the subject.

11. The method of claim 1, wherein the subject is a mammal.

12. The method of claim 11, wherein the mammal is a mammalian model of accelerated severe lupus nephritis (ASLN), which is characterized by acute onset of proteinuria, azotemia, autoantibody production, and development of severe nephritis.

13. The method of claim 12, wherein the mammalian model of accelerated severe lupus nephritis is induced by twice weekly injection with bacterial lipopolysaccharide (LPS).

14. The method of claim 13, wherein the bacterial lipopolysaccharide is a *Salmonella* type lipopolysaccharide.

15. The method of claim 1, wherein the herbal pharmaceutical composition is administered at a daily dosage at 12.5 g/kg body weight of the subject.

16. The method of claim 15, wherein the herbal pharmaceutical composition is administered daily for the first 2 days after the first injection of lipopolysaccharide.

* * * * *

SEQUENCE LISTING

```
<160> NUMBER OF SEQ ID NOS: 8

<210> SEQ ID NO 1
<211> LENGTH: 25
<212> TYPE: DNA
<213> ORGANISM: Artificial Sequence
<220> FEATURE:
<223> OTHER INFORMATION: IL-6 F
<220> FEATURE:
<221> NAME/KEY: misc_feature
<222> LOCATION: (1)..(25)

<400> SEQUENCE: 1
atgaagttcc tctctgcaag agact                                          25

<210> SEQ ID NO 2
<211> LENGTH: 24
<212> TYPE: DNA
```

```
<213> ORGANISM: Artificial Sequence
<220> FEATURE:
<223> OTHER INFORMATION: IL-6 R
<220> FEATURE:
<221> NAME/KEY: misc_feature
<222> LOCATION: (1)..(24)

<400> SEQUENCE: 2
cactaggttt gccgagtaga tctc                                          24

<210> SEQ ID NO 3
<211> LENGTH: 24
<212> TYPE: DNA
<213> ORGANISM: Artificial Sequence
<220> FEATURE:
<223> OTHER INFORMATION: IL-17A F
<220> FEATURE:
<221> NAME/KEY: misc_feature
<222> LOCATION: (1)..(24)

<400> SEQUENCE: 3
tccaccgcaa tgaagaccct gata                                          24

<210> SEQ ID NO 4
<211> LENGTH: 24
<212> TYPE: DNA
<213> ORGANISM: Artificial Sequence
<220> FEATURE:
<223> OTHER INFORMATION: IL-17A R
<220> FEATURE:
<221> NAME/KEY: misc_feature
<222> LOCATION: (1)..(24)

<400> SEQUENCE: 4
accagcatct tctcgaccct gaaa                                          24

<210> SEQ ID NO 5
<211> LENGTH: 23
<212> TYPE: DNA
<213> ORGANISM: Artificial Sequence
<220> FEATURE:
<223> OTHER INFORMATION: IL-18 F
<220> FEATURE:
<221> NAME/KEY: misc_feature
<222> LOCATION: (1)..(23)

<400> SEQUENCE: 5
actgtacaac cggagtaata cgg                                           23

<210> SEQ ID NO 6
<211> LENGTH: 20
<212> TYPE: DNA
<213> ORGANISM: Artificial Sequence
<220> FEATURE:
<223> OTHER INFORMATION: IL-18 R
<220> FEATURE:
<221> NAME/KEY: misc_feature
<222> LOCATION: (1)..(20)

<400> SEQUENCE: 6
tccatcttgt tgtgtcctgg                                               20

<210> SEQ ID NO 7
<211> LENGTH: 19
<212> TYPE: DNA
<213> ORGANISM: Artificial Sequence
<220> FEATURE:
<223> OTHER INFORMATION: GAPDH F
<220> FEATURE:
```

```
<221> NAME/KEY: misc_feature
<222> LOCATION: (1)..(19)

<400> SEQUENCE: 7
tccgcccctt ctgccgatg                                                    19

<210> SEQ ID NO 8
<211> LENGTH: 20
<212> TYPE: DNA
<213> ORGANISM: Artificial Sequence
<220> FEATURE:
<223> OTHER INFORMATION: GAPDH R
<220> FEATURE:
<221> NAME/KEY: misc_feature
<222> LOCATION: (1)..(20)

<400> SEQUENCE: 8
acggaaggcc atgccagtga                                                   20
```